(12) United States Patent
Yang et al.

(10) Patent No.: US 8,361,524 B2
(45) Date of Patent: Jan. 29, 2013

(54) MEDICINE TO TREAT DRUG ADDICTION AND PREPARATION METHOD THEREOF

(75) Inventors: Zheng Yang, Beijing (CN); Ming Fan, Beijing (CN); Jijun Chen, Cas (CN); Guozhang Jin, Pu (CN); Wuxian Ren, Shanxi (CN); Wei Feng, Sharod (CN)

(73) Assignees: Shanxi Yabad Pharmaceutical Group Corp., Shanxi (CN); Institute of Basic Medical Sciences, Academy of Military Medical Sciences, Beijing (CN)

( * ) Notice: Subject to any disclaimer, the term of this patent is extended or adjusted under 35 U.S.C. 154(b) by 0 days.

(21) Appl. No.: 12/940,695

(22) Filed: Nov. 5, 2010

(65) Prior Publication Data

US 2011/0111074 A1 May 12, 2011

Related U.S. Application Data

(62) Division of application No. 11/989,520, filed as application No. PCT/CN2006/001856 on Jul. 26, 2006, now abandoned.

(30) Foreign Application Priority Data

Jul. 26, 2005 (CN) .......................... 2005 1 0085531

(51) Int. Cl.
*A61K 36/00* (2006.01)
(52) U.S. Cl. ........................................ 424/773; 424/725
(58) Field of Classification Search .................. None
See application file for complete search history.

(56) References Cited

U.S. PATENT DOCUMENTS

| | | | |
|---|---|---|---|
| 2,206,407 A | 7/1940 | Kondo et al. | |
| 6,162,437 A | 12/2000 | Pyun et al. | |
| 6,218,541 B1 * | 4/2001 | Wang | 546/35 |

FOREIGN PATENT DOCUMENTS

| | | | |
|---|---|---|---|
| CN | 1174064 A | | 2/1998 |
| CN | 1439388 A | * | 9/2003 |
| CN | 1537549 A | | 10/2004 |
| CN | 1537550 A | | 10/2004 |
| WO | 2004/045505 A2 | | 6/2004 |

OTHER PUBLICATIONS

Liu (Acta Pharmacol Sin (1999), vol. 20, No. 11, pp. 1000-1004).*
Translation of CN 1439388 A—2003.*
Chen Jiaqiang: Journal of Sanming College, vol. 18, No. 4, Dec. 2001.

* cited by examiner

*Primary Examiner* — Susan Hoffman
(74) *Attorney, Agent, or Firm* — Birch, Stewart, Kolasch & Birch, LLP

(57) ABSTRACT

The present invention declares a pharmaceutical extract, composition that has effect to treat drug addiction, and its preparation method and quality control method. This extract is extracted from Radix Stephaniae Epigaeae. Starting medicine material of said composition is Radix Ginseng, Radix Astragali, Rhizoma Corydalis, Radix Angelicae Sinensis and Radix Ophiopogonis; and said composition also can prepared by ethanol extract of Radix Ginseng, ethanol extract of Radix Angelicae Sinensis, total alkaloids of Radix Stephaniae Epigaeae, water extract of Radix Astragali and water extract of Radix Ophiopogonis. Quality control method of said pharmaceutical composition includes one of or several of identifications and content determinations. The present invention also declares the use of said pharmaceutical extract, composition in the preparation of a medicine to treat drug addiction.

2 Claims, 4 Drawing Sheets

MEDICINE TO TREAT DRUG ADDICTION AND PREPARATION METHOD THEREOF

CROSS-REFERENCE TO RELATED APPLICATION

This application is a Divisional of U.S. application Ser. No. 11/989,520, filed on Mar. 13, 2008 now abandoned, which is the national phase under 35 U.S.C. §371 of PCT International Application No. PCT/CN2006/001856 which has an International filing date of Jul. 26, 2006, which designated the United States of America, which claims the priority of Chinese Application No. 2005-10085531.6, filed Jul. 26, 2005, all of which are hereby incorporated by reference as if fully set forth herein.

FIELD OF THE INVENTION

The present invention relates to a pharmaceutical extract, composition and its preparation method and quality control method, especially relates to a pharmaceutical extract, composition that has effect to treat drug addiction, and its preparation method and quality control method.

BACKGROUND OF THE INVENTION

In recent years, substance abuse in our country has become a serious social problem, and the drug abuse population rises year by year. The heroin abuse population who has only registered by the public security department is more than one million, and the actual population even more than that. In recent years, the population abusing amphetamines stimulant narcotics also rises rapidly at increasing trend on young people of our country. Once catch narcotic, one will become addict to it soon. It not only impairs health, but also wastes money. Gradually, it often makes the evil consequence that the family was broken up. Regardless using which medicine to treat drug addiction on early phase, relapse rate is still up to 95%. The long-term drug addict exists the lasting psychic dependence (psychology addiction), and deferment of the protracted withdrawal symptom is also an important reason to cause relapse. Now, still without an especially effective medicine specially uses to maintenance treatment for drug addiction on late phase.

In patent CN1537549A and CN1537550A, the declarer developed the traditional Chinese medicine compound prescription preparation which is prepared by five traditional Chinese medicine extracts of Radix Ginseng, Radix Astragali, Rhizoma Corydalis, Radix Angelicae Sinensis, Radix Ophiopogonis. According to the characteristics of chemical constituents in each starting medicine material and dosage form, extract medicines by classification: extract Radix Ginseng and Radix Angelicae Sinensis by ethanol reflux extraction process; extract effective ingredients of Radix Astragali and Radix Ophiopogonis by water-extraction and ethanol-precipitation process respectively; gain effective ingredients, effective alkaloids, from Rhizoma Corydalis by diafiltration with the acid solution, then basification and ethanol recrystallization. These extracts compose the traditional Chinese medicine compound prescription preparation, which has preferable curative effect to treat stimulant withdrawal symptom and treat protracted withdrawal symptom of opioids addiction.

But there is no stepholidine in Rhizoma Corydalis, which tetrahydropalmatine extracted from is raceme dl-THP, and it must further split racemes to get L-THP. On the other hand, the content of raceme dl-THP contained in Rhizoma Corydalis is rather low, moreover, dosage of Rhizoma Corydalis in this drug addiction treatment prescription is large, Rhizoma Corydalis mainly depends on the artificial cultivation, its output is low, its cost is high, and it cannot meet the need of industrialization large production.

SUMMARY OF INVENTION

The purpose of the present invention is to provide a pharmaceutical extract which has effect to treat drug addiction; another purpose of the present invention is to provide a pharmaceutical composition which has effect to treat drug addiction; the third purpose of the present invention is to provide the preparation method and quality control method of this composition.

The purposes of present invention can be implemented through the following technical schemes:

Total alkaloids of Radix Stephaniae Epigaeae, the total alkaloids are produced by the following methods:

Pulverize Radix Stephaniae Epigaeae to coarse power, add 35-100% ethanol at 4-10 times amount of stating material's, extract by reflux extraction from one to four times, 1-3 hours each time, filter, combine the filtrates of ethanol extract, recover ethanol, then concentrate to obtain the thick extract with relative density of 1.18-1.30 at 80° C.; acidify this thick extract until the pH value up to 1-4 by 3-18% HCl solution, filter, basify the filtrate until the pH value up to 8-11 by 8-20% NaOH solution, stand, collect the precipitate, wash the precipitate with water by filter, take the precipitate, dry it, then obtain total alkaloids of Radix Stephaniae Epigaeae.

Preferable preparation method of total alkaloids of Radix Stephaniae Epigaeae is as follows:

Pulverize Radix Stephaniae Epigaeae to coarse power, add ethanol at 5 times amount of stating material's, extract by reflux extraction twice, 2 hours each time, filter, combine the filtrates of ethanol extract, recover ethanol, then concentrate to obtain the thick extract with relative density of 1.18-1.30 at 80° C.; acidify this thick extract until the pH value up to 2-3 by 5% HCl solution, filter, basify the filtrate until the pH value up to 9-10 by 10% NaOH solution, stand, collect the precipitate, wash the precipitate with water by filter, take the precipitate, dry it, then obtain total alkaloids from Radix Stephaniae Epigaeae.

The present invention declares a pharmaceutical composition that has effect to treat drug addiction, and starting material of this traditional Chinese medicine composition is composed of as follows:

| | |
|---|---|
| Radix Ginseng | 1-10 parts by weight |
| Radix Stephaniae Epigaeae | 50-60 parts by weight |
| Radix Astragali | 3-40 parts by weight |
| Radix Angelicae Sinensis | 2-25 parts by weight |
| Radix Ophiopogonis | 1-10 parts by weight |

Preferably, the said starting material is composed of:

| | |
|---|---|
| Radix Ginseng | 1 parts by weight |
| Radix Stephaniae Epigaeae | 35 parts by weight |
| Radix Astragali | 7 parts by weight |
| Radix Angelicae Sinensis | 8 parts by weight |
| Radix Ophiopogonis | 2 parts by weight; |
| Radix Ginseng | 8 parts by weight |
| Radix Stephaniae Epigaeae | 12 parts by weight |
| Radix Astragali | 13 parts by weight |

-continued

| | |
|---|---|
| Radix Angelicae Sinensis | 5 parts by weight |
| Radix Ophiopogonis | 8 parts by weight; |
| Radix Ginseng | 5 parts by weight |
| Radix Stephaniae Epigaeae | 26 parts by weight |
| Radix Astragali | 20 parts by weight |
| Radix Angelicae Sinensis | 5 parts by weight |
| Radix Ophiopogonis | 5 parts by weight; |
| Radix Ginseng | 3 parts by weight |
| Radix Stephaniae Epigaeae | 16 parts by weight |
| Radix Astragali | 10 parts by weight |
| Radix Angelicae Sinensis | 5 parts by weight |
| Radix Ophiopogonis | 3 parts by weight; |
| Radix Ginseng | 8 parts by weight |
| Radix Stephaniae Epigaeae | 40 parts by weight |
| Radix Astragali | 25 parts by weight |
| Radix Angelicae Sinensis | 10 parts by weight |
| Radix Ophiopogonis | 8 parts by weight. |

Through scientific extract and refine, add general adjuvant, according to usual process, starting material of this invention pharmaceutical composition is produced to clinic or pharmaceutical acceptable dosage forms, for example: tablet, capsule, soft capsule, drop pill, pill, granule, honey refined extract, sustained-release preparation, rapid-release preparation, controlled-release preparation, oral liquid or injection.

This invention provides a preparation method of the said pharmaceutical composition preparation:

A. Pulverize Radix Stephaniae Epigaeae to coarse power, add 35-100% ethanol at 4-10 times amount of stating material's, extract by reflux extraction from one to four times, 1-3 hours each time, filter, combine the filtrates of ethanol extract, recover ethanol, then concentrate to obtain the thick extract with relative density of 1.18-1.30 at 80° C.; acidify this thick extract until the pH value up to 1-4 by 3-18% HCl solution, filter, basify the filtrate until the pH value up to 8-11 by 8-20% NaOH solution, stand, collect the precipitate, wash the precipitate with water by filter, take the precipitate, dry it, then obtain total alkaloids of Radix Stephaniae Epigaeae, stand it by service;

B. Add 35-95% ethanol at 4-10 times amount to Radix Ginseng, Radix Angelicae Sinensis, then extract by reflux extraction from one to three times, 1-4 hours each time, combine the filtrates of ethanol extract, recover ethanol, then concentrate to obtain the thick extract I with relative density of 1.18-1.30 at 80° C., stand it by service; decoct Radix Astragali and Radix Ophiopogonis with water at 5-10 times amount from one to four times, 1-3 hours each time, combine all the decoction, filter, concentrate the filtrate to obtain the thick extract with relative density of 1.18-1.30 at 80° C., add ethanol until ethanol concentration up to 50-90%, stand, filter, take the filtrates, recover ethanol, then concentrate to obtain the thick extract II with relative density of 1.18-1.30 at 80° C., stand it by service;

C. Take said total alkaloids of Radix Stephaniae Epigaeae, the thick extract I, the thick extract II, combine them, add general adjuvant, mix uniformly, according to usual process, produce to tablet, capsule, soft capsule, drop pill, pill, granule, honey refined extract, sustained-release preparation, rapid-release preparation, controlled-release preparation, oral liquid or injection.

Preferably, a preparation method of the pharmaceutical composition preparation is:

A. Add 5 times amount ethanol to Radix Stephaniae Epigaeae, then extract by reflux extraction for three times, 1 hour each time, filter, combine the filtrates of ethanol extract, recover ethanol, then concentrate to obtain the thick extract is with relative density of 1.22 at 80° C.; acidify this thick extract until the pH value up to 2-3 by 5% HCl solution, filter, basify the filtrate until the pH value up to 9-10 by 10% NaOH solution, stand, collect the precipitate, wash the precipitate with water by filter, take the precipitate, dry it, then obtain total alkaloids from Radix Stephaniae Epigaeae, stand it by service;

B. Add 60% ethanol at 5 times amount to Radix Ginseng, Radix Angelicae Sinensis, then extract by reflux extraction for three times, 2 hours each time, combine the filtrates of ethanol extract, recover ethanol, then concentrate to obtain the thick extract I with relative density of 1.18-1.22 at 80° C., stand it by service; decoct Radix Astragali and Radix Ophiopogonis with water at 6 times amount for three times, 2 hours each time, combine all the decoctions, filter, concentrate the filtrate to obtain the thick extract with relative density of 1.22 at 80° C., add ethanol until ethanol concentration up to 80%, stand still, filter, take the filtrates, recover ethanol, then concentrate to obtain the thick extract II with relative density of 1.22 at 80° C., stand it by service;

C. Take the said total alkaloids of Radix Stephaniae Epigaeae, the thick extract I, the thick extract II, combine them, add 1-10% sodium carboxymethyl starch, mix uniformly, recover solvent until dry, dry at 80° C. or dry by vacuum, crush and sieve, make granules, press tablet, coating.

The present invention also provides starting material of a pharmaceutical composition is composed of as follows:

| | |
|---|---|
| ethanol extract of Radix Ginseng | 5-15 parts by weight |
| ethanol extract of Radix Angelicae Sinensis | 20-40 parts by weight |
| total alkaloids of Radix Stephaniae Epigaeae | 5-15 parts by weight |
| water extract of Radix Astragali | 20-60 parts by weight |
| water extract of Radix Ophiopogonis | 5-15 parts by weight. |

Preferably, the said starting material is composed of:

| | |
|---|---|
| ethanol extract of Radix Ginseng | 11 parts by weight |
| ethanol extract of Radix Angelicae Sinensis | 31 parts by weight |
| total alkaloids of Radix Stephaniae Epigaeae | 10 parts by weight |
| water extract of Radix Astragali | 36.5 parts by weight |
| water extract of Radix Ophiopogonis | 11 parts by weight; |
| ethanol extract of Radix Ginseng | 5 parts by weight |
| ethanol extract of Radix Angelicae Sinensis | 16 parts by weight |
| total alkaloids of Radix Stephaniae Epigaeae | 20 parts by weight |
| water extract of Radix Astragali | 40 parts by weight |
| water extract of Radix Ophiopogonis | 19 parts by weight; |
| ethanol extract of Radix Ginseng | 15 parts by weight |
| ethanol extract of Radix Angelicae Sinensis | 30 parts by weight |
| total alkaloids of Radix Stephaniae Epigaeae | 15 parts by weight |
| water extract of Radix Astragali | 30 parts by weight |
| water extract of Radix Ophiopogonis | 10 parts by weight. |

Ginsenoside content in the said ethanol extract of Radix Ginseng is not less than 50 g/Kg; angelica lactone content in the ethanol extract of Radix Angelicae Sinensis is not less than 2 g/Kg; (−) tetrahydropalmatine content in the total alkaloids of Radix Stephaniae Epigaeae is not less than 20%; astragaloside content in the water extract of Radix Astragali is not less than 0.2 g/Kg; ophiopogonin content in the water extract of Radix Ophiopogonis is not less than 0.9 g/Kg.

Radix Ginseng in starting material of the said invention pharmaceutical composition can replace with equal weight parts Radix Panacis Quinquefolii, and ethanol extract of Radix Ginseng can replace with extract of Radix Panacis Quinquefolii. Radix Stephaniae Epigaeae in the said invention pharmaceutical composition preferably chooses Stephania delavayi Diels from Mentspermaceae.

Quality control method of this invention pharmaceutical composition preparation include following identification and/or content determination.

Identification include one of or several following methods:

A. Take 3.5 g-6 g capsule, pill, tablet, granule, honey refined extract, sustained-release preparation or rapid-release preparation of the pharmaceutical composition, grind fine, add methanol 50 ml, heat and reflux for 30 minutes, take it out, stand it cold, filter, evaporate filtrate 20 ml until dry, add 10 ml water and 5 drops hydrochloric acid into residue, shake up, extract twice by adding ethyl ether, 15 ml each time, combine ether extract, stand it by service; add ammonia to water layer until pH≈10, shake up, extract twice by adding chloroform, 20 ml each time, remove chloroform extract, extract for three times by adding n-butyl alcohol saturated with water to water layer, 20 ml each time, combine n-butyl alcohol extract, wash for three times by adding ammonia reagent, 10 ml dosage each time, take n-butyl alcohol extract, evaporate until dry, dissolve residue by add 1 ml methanol into it, as test sample solution; take Ginsenoside Rb1 and Ginsenoside Rg1 respectively as reference substance, add methanol to produce mix solution containing 1 mg reference substance per 1 ml respectively, as reference substance solution;

According to the thin layer Chromatography test, 5~10 μl each of the said two solutions were loaded onto the same TLC plate of silica gel G respectively, the upper layer solution is a mixture of n-butyl alcohol, ethyl acetate and water (4:1:5), according to ratio 10:1, a mix solution of this upper layer solution and methanol is used as developer, in developing, the development chamber is saturated by ammonia for 30 minutes, and developed distance is more than 15 cm, the plate was removed and air dried, and sprayed with ethanol solution of 10% sulfuric acid, then heated in 105° C. until visualize the chromatogram, the chromatogram produced by the test sample solution showed the same color spots as that displayed by the two reference substance solutions in their respectively corresponding areas;

B. Take astragaloside reference substance, add methanol to produce mix solution containing 1 mg reference substance per 1 ml, as reference substance is solution, according to the thin layer Chromatography test, 5~10 μl each of reference substance solutions and test sample solutions produced by the identification method A are respectively loaded onto the same TLC plate of silica gel G, the upper layer solution is a mixture of n-butyl alcohol, ethyl acetate and water (4:1:5), according to ratio 10:1, a mix solution of this upper layer solution and methanol is used as developer, in developing, the development chamber is saturated by ammonia for 30 minutes, and developed distance is more than 15 cm, the plate was removed and air dried, and sprayed with ethanol solution of 10% sulfuric acid, then heated in 105° C. until visualize the chromatogram, the chromatogram produced by the test sample solution showed the same color spots as that displayed by the two reference substance solutions in their respectively corresponding areas;

C. Produce ethyl ether extract according to the identification A method, evaporate solvent to dry, dissolve residue by adding 1 ml ethyl acetate, as test sample solution; take another 0.5 g reference starting material of Radix Angelicae Sinensis, add ethyl ether 20 ml, heat and reflux for 1 hour, filter, evaporate ethyl ether in filtrate to dry, produce reference starting material solution by same method; according to the thin layer Chromatography test, 5~10 μl of the said two solutions is loaded onto the same TLC plate of silica gel G respectively, a mixture of hexane and ethyl acetate (9:1) is used as developer, after development, the plate was removed and dried in air, and it was exam under 365 nm ultraviolet lamp, the chromatogram produced by the sample solution showed the same color spots as that displayed by the two reference substance solutions in their respectively corresponding areas;

D. Take 1.75-3.5 g capsule, pill, tablet, granule, honey refined extract, sustained-release preparation or rapid-release preparation of a pharmaceutical composition, grind fine, decoct by adding water 100 ml for 30 minutes until rest volume up to 20 ml, stand it cold, add methanol until methanol content up to 50%, shake up, stay for 1 hour at lower than 10° C., filter, pressure reduction concentrate the filtrate to dry, dissolve the residue by adding 10 ml water, add 2 ml hydrochloric acid, shake up, reflux with boil water bath for 1 hour, take out and stand it cold, extract twice by ethyl ether, dosage 25 ml, combine ethyl ether extract, stand for 30 minutes, evaporate solvent until dry, dissolve residue by adding 1 ml methanol, shake up, as test sample solution;

take another 0.5 g reference drug of Radix Ophiopogonis, add water 20-30 ml, boil for 10 minutes, filter, produce reference starting material solution by same method; according to the thin layer Chromatography test, 2~5 μl each of the said two solutions is loaded onto the same TLC plate of silica gel G respectively, a mixture of chloroform and acetone (4:1) is used as developer. After development, the plate was removed and air dried, and sprayed with ethanol solution of 10% sulfuric acid, then heated in 105° C. until visualize the chromatogram, the chromatogram produced by the test sample solution showed the same color spots as that displayed by the two reference substance solutions in their respectively corresponding areas.

Content determination in quality control method is as follows:

An Applicability Test of Chromatogram Condition and System

Use octadecylsilanized silica gel as packing; add ammonia 0.025 mol/L into potassium dihydrogen phosphate and acetonitrile (1:1) solution until as the mobile phase; detection wavelength is 225 nm, theoretical plate number counted according to (−) tetrahydropalmatine peak is not less than 3000;

Preparation of Reference Substance Solution

Pressure reduction dry 5.5 mg (−) tetrahydropalmatine reference substance at 60° C. until constant weight, weight it accurately, put it into 10 ml volumetric flask, dissolve by methanol, dilute to the volume, shake up, measure 1 ml the said solution accurately, put it into 10 ml volumetric flask, and dilute with the mobile phase to the volume, shake up, that is;

Preparation of Test Sample Solution

Accurately weight 0.35-0.45 g capsule, pill, tablet, granule, honey refined extract, sustained-release preparation or rapid-release preparation of the said pharmaceutical composition, grind fine, put it into conical flask, add 50 ml methanol accurately, shake up, weight it up, put it into ultrasonic cleaner, deal with ultrasound for 30 minutes, take it out, complement weight with methanol, shake up, filter, abandon first filtrate, measure 1 ml the following filtrate accurately and put it into 10 ml volumetric flask, dilute with the mobile phase to the volume, shake up, filter it with 0.45 μm microporous membrane filter, take the following filtrate as test sample solution;

Determination Method

Accurately suck reference substance solution and test sample solution 10 μl respectively, inject into liquid chromatogram instrument, determine, that is;

(−) Tetrahydropalmatine regarded as Radix Stephaniae Epigaeae is not less than 20 mg in each of 0.35-0.45 g capsule, pill, tablet, granule, honey refined extract, sustained-release preparation or rapid-release preparation of the said pharmaceutical composition.

Preferably, the extract efficiency of extracting THPBs and L-THP from Radix Stephaniae Epigaeae in the present invention is rather high, and it reduces processes of extracting raceme tetrahydropalmatine dl-THP from Rhizoma Corydalis and further split raceme to gain L-THP. Raceme dl-THP content in Rhizoma Corydalis is rather low, on the other hand, and tetrahydropalmatine is effective analgesia ingredient in the traditional Chinese medicine, Rhizoma Corydalis (Corydalis ambigua Cham. et Sch), but its practice content is very low. Alkaloid extract efficiency of Caulis Fibraureae (Fibraurea recisa Pierre) is up to 6%, and it can be transformed to raceme tetrahydropalmatine through deoxidation reaction, but effective analgesia ingredient is (−)tetrahydropalmatine, and it must further split raceme to gain L-THP, and there is no Stepholidine. Radix Stephaniae Epigaeae is from Stephania delavayi Diels from Mentspermaceae, in which can extract alkaloid 3-4%, main ingredients in it is (−)-tetrahydropalmatine, (−) stepholidine and (−) corydalmine and so on have the most distinctive pharmacological effect. The said inventive extract technic for total alkaloids of Radix Stephaniae Epigaeae is simple, stable, easy control. Gain efficiency of THPBs is high, so it reduces cost of pharmaceutical manufacture. The said inventive total alkaloids of Radix Stephaniae Epigaeae has drug abstain effect, can mostly raise expression of Penk mRNA or expression of POMC mRNA in arcuate nucleus.

Combined with the other starting material which are Radix Ginseng, Radix Astragali, Radix Angelicae Sinensis, Radix Ophiopogonis in this invention, effective alkaloids extracted with high efficiency from Radix Stephaniae Tetrandrae and Radix Stephaniae Epigaeae belonging to traditional Chinese medicines of Stephaniae subgenus are produced traditional Chinese medicine compound prescription to treat drug addiction. The examination testifies that combinations between Radix Stephaniae Epigaeae and the said invention composition, or total alkaloids of Radix Stephaniae Epigaeae and the said invention extract composition have synergistic effect, and this synergistic effect reduces side effects induced by only using total alkaloids of Radix Stephaniae Epigaeae with more prominent therapeutic effect. The examination also testifies that this invention composition has more prominent curative effect than composition prescription (Guiyuan Tablet) containing Rhizoma Corydalis.

Synergistic effect of this invention pharmaceutical composition mainly indicates: block gain and expression of mouse morphine behavioral sensitization, inhibit formation and expression of morphine behavioral sensitization, prevent formation of morphine addicted behavior, inhibit sensitization behavior induced by morphine; reduce mouse's activity, inhibit acute high activity effect of methyl benzedrine; also block gain and expression of mouse methyl benzedrine behavioral sensitization. It has been proved that it can inhibit reward effect of methyl benzedrine, intervene intravenous self-administration relapse behavior of morphine abusive rat induced by environment, with combinations between Radix Stephaniae Epigaeae, Radix Ginseng, Radix Astragali, Radix Angelicae Sinensis and Radix Ophiopogonis; or effective alkaloids and extract of Radix Ginseng, Radix Astragali, Radix Angelicae Sinensis and Radix Ophiopogonis. It is proved that this invention pharmaceutical composition preparation has effect of analgesia, sedation, prolong the sleeping time, anti-anxiety effects by animal pharmacodynamics experiment.

By experiment, this invention pharmaceutical composition preparation is proved that it has drug abstinence, alleviates symptom, psychology craving inhibition, relapse reducing effects for dependence or addiction inducing by opioids substances, including heroin, morphine, pethidne, methadone, and so on, as well as other spiritual active materials (including cocaine, benzedrines stimulant, wine, smoke, cannabis, sedatives and hypnotics, and so on).

At the same time, the present invention indicates that Stephania delavayi Diels from Mentspermaceae has prominent effect in medicines to treat drug addiction.

The following experiments and examples will further illustrate but not mean to limit the present invention.

Experiment 1

Isolate (−) Tetrahydropalmatine from Radix Stephaniae Epigaeae and Identification Experiment 1. Isolation Method for Total Alkaloids of Radix Stephaniae Epigaeae and (−) Tetrahydropalmatine from Radix Stephaniae Epigaeae Extract for THPBs, effective total alkaloids of Radix Stephaniae Epigaeae, air dry and pulverize Radix Stephaniae Epigaeae to get 300 g starting material powder, reflux with 85% ethanol for three times, add 1500 mL ethanol each time, reflux for 1 hour to gain tetrahydroprotoberberines (THPBs) alkaloid solution extracted from Radix Stephaniae Epigaeae, then recover ethanol and concentrate to obtain the thick extract 100 ml with relative density of 0.905 at 80° C. Acidify the thick extract until the pH value up to 2 by 5% HCl solution, filter off insoluble substances, basify the acid filtrate until the pH value up to 10 by 10 NaOH solution, stand, collect the precipitate, wash the precipitate with moderate amount water, take the precipitate, dry it, then dry the precipitate to obtain 14.7 g total alkaloids of Radix Stephaniae Epigaeae.

Dissolve the total alkaloids of Radix Stephaniae Epigaeae with 50 ml ethanol, stand at room temperature, and precipitate crystal 6.0 g. Recrystallize it again with ethanol to gain 3.5 g L-tetrahydropalmatine, and yield rate is 1.12%.

Ultraviolet spectrum identification: instrument: Shimazu 210A UV-spectrophotometer. Solvent is ethanol, and determination data of UV map: UV λmax MeOH (log ε) nm: 210 (4.46), 219 (sh, 4.23), 281 (3.72). Analysis: B strap of aromatic ring at 210 nm, K strap of aromatic ring at 219 nm, characteristic absorption signal at 281 nm.

Infrared absorption spectrum (IR) identification: instrument: Bio-Red FTS-135 IR-spectrophotometer. Determination condition: pressing potassium bromide troche. Analysis: 3612 $cm^{-1}$:—OH stretching vibration. 2950, 2920 $cm^{-1}$: CH stretching vibration. 1626 and 1515, 1461 $cm^{-1}$: characteristic absorption signal of aromatic ring. 863, 811 $cm^{-1}$: strong absorption, fingerprint signal of substituted aromatic ring.

TABLE 1

| Absorption peak ($cm^{-1}$) | Vibration type | Group | Intensity of absorption peak |
|---|---|---|---|
| 3612 | vOH | —OH | s |
| 2950, 2920 | vCH | $CH_2$ | m |
| 1620, | vC=C | C=C | w |
| 1515, 1461 | vC=C | C=C | s |
| 863, 811 | | | m |

Mass spectrum (EIMS) identification: instrument: AUTO SPEC3000 mass spectrograph. Condition: fast atom bombardment EI-MS (20 eV). Determination data m/z (relative intensity %): m/z 355 ($M^+$, 100), 340 [$(M-Me)^+$, 10], 324 [$(M-OMe)^+$, 18], 190 (25), 164 (72), 149 (48), 121 (15). 3.

Analysis: a.m/z 355 is fragment ion peak of this molecule, corresponding molecular formula is $C_{21}H_{25}NO_4$; b. m/z 340 is fragment ion peak of this molecule losing a methyl, and it indicates existence of methyl. c.m/z 324 is fragment ion peak of this molecule losing a methoxy, it indicates existence of methoxy.

$^1H$ nuclear magnetic resonance spectra ($^1H$ NMR): instrument: Bruker DR-500 superconductor nuclear magnetic resonance spectrometer. Condition: solvent is $CDCl_3$, internal standard is TMS, determine at 500 MHz frequency. Analysis: a. δ6.82 (1H, d, J=8.3 Hz), 6.73 (1H, d, J=8.3 Hz) indicate existence of proton at ortho position of aromatic ring, corresponding to H-11 and H-12. b. δ6.63 (1H, s), 6.57 (1H, s) indicate existence of two hydrogen atoms without protons at ortho position of aromatic ring, corresponding to H-1 and H-4. c. δ3.83 (3H, s), 3.80 (6H, s), 3.78 (3H, s) indicate existence of four methoxies.

TABLE 2

| Sequence number of proton | Chemical shift | Multi-storage degree | Coupling constant (JHz) | Proton number | Corresponding proton |
|---|---|---|---|---|---|
| 1 | 6.63 | s | | 1 | —C=CH— |
| 4 | 6.57 | s | | 1 | —C=CH— |
| 5 | 2.78 | m | | 1 | CHax—N— |
| 5 | 2.58 | m | | 1 | CHeq—N— |
| 6 | 3.09 | m | | 1 | —CHeq—N— |
| 6 | 2.62 | m | | 1 | —CHax—N— |
| 8 | 4.20 | d | 15.7 | 1 | —CH$_{eq}$—N— |
| 8 | 3.49 | d | 15.7 | 1 | —CH$_{ax}$—N— |
| 11 | 6.73 | d | 8.3 | 1 | —C=CH— |
| 12 | 6.82 | d | 8.3 | 1 | —C=CH— |
| 13 | 2.79 | dd | 15.7, 12.1 | 1 | CHax—N— |
| 13 | 3.20 | dd | 15.7, 8.0 | | CHeq—N— |
| 13a | 3.48 | br.d | 12.8 | 1 | CH—N— |
| OMe | 3.83 | s | | 3 | OMe |
| OMe | 3.80 | s | | 6 | OMe × 2 |
| OMe | 3.78 | s | | 3 | |

$^{13}C$ nuclear magnetic resonance spectra ($^{13}C$ NMR):
instrument: Bruker DRX-500 superconductor nuclear magnetic resonance spectrometer.
Determination condition: solvent is $C_5D_5N$, and internal standard is TMS, determining at 125 MHz frequency.
Determination data: list in the following tablet.

TABLE 3

| Sequence number of carbon atom | Determination value of (−) tetrahydropalmatine |
|---|---|
| 1 | 108.4d |
| 1a | 129.4s |
| 2 | 147.2s |
| 3 | 147.3s |
| 4 | 111.1 |
| 4a | 126.5s |
| 5 | 28.8t |
| 6 | 51.3t |
| 8 | 53.7t |
| 8a | 127.4s |
| 9 | 150.0s |
| 10 | 144.8s |
| 11 | 110.8d |
| 12 | 123.7d |
| 12a | 128.3s |
| 13 | 36.0t |
| 13a | 59.1 |
| OMe | 55.6q |
| OMe | 55.6q |
| OMe | 55.8q |
| OMe | 59.9q |

Comprehensive analysis indicates: this compound shows positive to modified bismuth potassium iodide test solution, so it is alkaloid. EI-MS mass spectrum determines that its molecule-ion peak is ink 355, corresponding to $C_{21}H_{25}NO_4$, and it indicates this compound molecular composition is right. The UV-spectrum shows existence of aromatic ring in this compound molecule. For this compound, IR 3612 cm$^{-1}$ indicates existence of hydroxyl in molecule, and 1626, 1515 and 1461 cm$^{-1}$ indicate existence of aromatic ring in molecule. 5. 1H NMR of this compound give various related characteristic resonates signal, corresponding to (−) tetrahydropalmatine. $^{13}C$ NMR of this compound provides 21 carbon atom signals, and you can further identify characters of each carbon atom by combining with $^{13}C$ NMR DEPT spectrum, corresponding to (−)-tetrahydropalmatine. The physical properties, melting point and optical value of this compound are corresponding to (−)-tetrahydropalmatine. In summary, this compound structure is (−)-tetrahydropalmatine, English name: (−)-tetrahydropalmatine, molecular formula: $C_{21}H_{25}NO_4$, molecular weight: 355.4275.

Experiment 2

Purity Determination of (−)-Tetrahydropalmatine
Isolated from Radix Stephaniae Epigaeae Silica Gel Thin Layer Plate (TLC GF254) Determination
a. (−)-Tetrahydropalmatine extract in experiment 1, produce 1 ml test sample methanol solution contain 1000 mg (−)-tetrahydropalmatine, dot 10 μl, 20 μl, 30 μl quantitatively on Silica gel thin layer plate, develop with acetone-benzene (2:8, v/v), developed distance is 8.0 cm, visualize the chromatogram with modified bismuth potassium iodide test solution. Only range red spot at 4.8 cm place (Rf value=4.8/8.0=0.60), there is no spot of impurity in the to chromatograph.
b. Produce 1 ml test sample methanol solution contain 1000 mg (−)-tetrahydropalmatine, dot 10 μl, 20 μl, 30 μl quantitatively on Silica gel thin layer plate, develop with methanol-benzene (1:12, v/v), developed distance is 8.0 cm, visualize the chromatogram with modified bismuth potassium iodide test solution. Only range red spot at 5.0 cm place (Rf value=5.0/8.0=0.63), there is no spot of impurity in the chromatograph.
c. Produce 1 ml test sample methanol solution contain 1000 mg (−)-tetrahydropalmatine, dot 10 μl, 20 μl, 30 μl quantitatively on Silica gel thin layer plate, develop with petroleum ether-ether (1:3, v/v), (the development chamber is saturated by concentrated ammonia for 15 minutes before development.) developed distance is 8.0 cm, visualize the chromatogram with modified bismuth potassium iodide test solution. Only range red spot at 4.2 cm place (Rf value=4.2/8.0=0.52), there is no spot of impurity in the chromatograph.
Highly Effective Liquid Phase Determination
Sample preparation: accurately take 0.00201 g prepared (−) tetrahydropalmatine, add solvent until volume up to 2.0 mL in volumetric flask, its concentration is 1.05 mg/mL. b. Chromatograph condition: instrument: Waters 2996, (US), diode array detector; chromatographic column: Waters ODS2 (3.9×150 Mm, 5 μm). Mobile phase: acetonitrile-water (40:60), flow rate: 1 mL/min; detection wavelength: 225 nm, column temperature: 35° C., injection volume: 30 μl.

TABLE 4

| Sequence number of peak | Retention time | Peak area | Area % |
|---|---|---|---|
| 1 | 6.309 | 10660 | 0.03 |
| 2 | 9.279 | 36502681 | 99.97 |

Result Analysis:

The result indicates that purity of (−) tetrahydropalmatine extracted from Radix Stephaniae Epigaeae is 99.97%, and it conforms to the standard purity requirement.

Experiment 3

Isolate Each Compound in Radix Stephaniae Epigaeae and Identification Experiment Isolate each compound in Radix Stephaniae Epigaeae: air dry and pulverize Radix Stephaniae Epigaeae to get 300 g starting material powder, reflux with ethanol for three times, add 1500 mL ethanol each time, reflux for 2 hours, then recover ethanol and concentrate to obtain the thick extract 100 ml (relative density 0.905, 80° C.). Acidify the thick extract until the pH value up to 2 by 5% HCl solution, filter off the insoluble substances, basify the acid filtrate until the pH value up to 10 by 10% NaOH solution, stand, collect the precipitate, wash the precipitate with moderate amount water, take the precipitate, dry it, then dry the precipitate to obtain 14.7 g total alkaloids of Radix Stephaniae Epigaeae.

Dissolve the total alkaloids of Radix Stephaniae Epigaeae with 50 ml ethanol, stand at room temperature, and precipitate crystal 6.0 g. Recrystallize it again with ethanol to gain 3.5 g L-tetrahydropalmatine, and yield rate is 1.12%. Gain 8.5 g by combining mother liquor and recovering solvent until dry, dissolve by chloroform, absorb on 16 g silica gel, evaporate to dry at room temperature, chromatographic analysis by silica gel column (200 g), gradient elute by chloroform-methanol (100: 0-90-10, v/v), each fraction is 100 ml, combine the fractions 3-6 to get L-tetrahydropalmatine (1, L-tetrahydropalmatine, 200 mg), combine the fractions 10-12 to get corydalmine (2, corydalmine, 25 mg), combine the fractions 14-18 to get stepholidine (3, stepholidine, 20 mg).

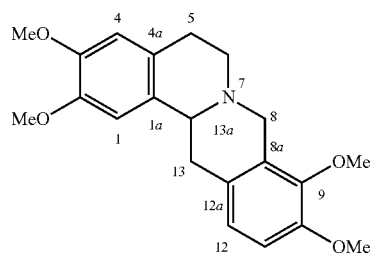

1

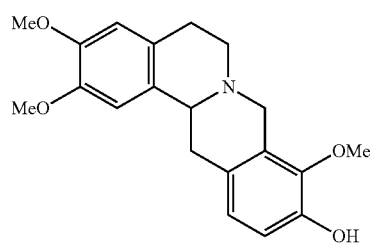

2

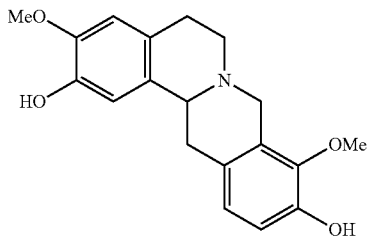

3

Structure Identification

Structure Identification of (L)-Corydalmine (2, Corydalmine)

Light yellow crystal (methanol), mp. 176-179° C., $[\alpha]_D$, −289° (0.4, EtOH). EI-MS m/z (%): 341) (M+) (27, 326 (MA)+, (55), 324 (22), 310 (37), 295 (18), 155 (21). 139 (24), 125 (41), 111 (57), 99 (34), 97 (77), 95 (37), 85 (75), 81 (27), 71 (83), 69 (52), 57 (100). $^1$H NMR (400 MHz, CDCl$_3$) δ: 6.81 (1H, d, J=8.3 Hz, H-12), 6.77 (1H, d, J=8.3 Hz, H-11), 6.73, 6.62 (1H, s, H-1, H-4 respectively), 4.22 (1H, d, J=15.4 Hz, Ha-8), 3.57 (1H, d, J=14.9 Hz, Hb-8). 3.89, 3.87, 3.81 (3H, s, OCH$_3$ respectively). $^{13}$C NMR (DEPT) (100 MHz, CDCl$_3$) δ: 108.5 (d, C-1), 147.5 (s, C-2), 146.5 (s, C-3), 114.3 (d, C-4), 126.6 (s, C-4a), 29.0 (t, C-5), 51.6 (t, C-6), 53.8 (t, C-8), 127.2 (s, C-8a), 143.3 (s, C-9), 147.5 (C-10), 111.3 (d, C-11), 124.8 (d, C-12), 127.9 (s, C-12a), 36.2 (t, C-13), 59.4 (C-13a), 55.8 (q, OCH$_3$), 56.1 (q, OCH$_3$), 60.6 (q, OCH$_3$). The said data is corresponding to corydalmine's, so compound 2 is identified as corydalmine.

(L)-Stepholidine (Stepholidine, 3)

Light yellow crystal (methanol), mp. 1253-128° C., [α], −305° (0.6, EtOH). EI-MS m/z (%): 328 (M+1)+ (9), 327 (M+) (77), 326 (M−1)+ (48), 296 (12), 179 (14), 178 (100), 163 (18), 150 (27), 149 (29), 135 (30), 121 (11), 107 (12), 91 (8), 77 (13). $^1$H NMR (400 MHz, CD$_3$OD) δ: 6.79 (1H, d, J=8.5 Hz, H-12), 6.76 (1H, s, H-1), 6.72 (1H, d, J=8.5 Hz, H-11), 6.66 (H, s, H-4), 4.18 (1H, d, J=15.3 Hz, Ha-8), 3.51 (1H, d, J=15.3, Hz, Hb-8). 3.81, 3.80 (3H, s, 2×OMe respectively). $^{13}$C NMR (DEPT) (100 MHz, CD$_3$OD) δ: 113.2 (d, C-1), 148.2 (s, C-2), 146.1 (s, C-3), 116.5. (d, C-4), 126.3 (s, C-4a), 29.3 (t, C-5), 52.8 (t, C-6), 54.8 (t, C-8), 127.3 (s, C-8a), 145.10 (s, C-9), 147.9 (s, C-10), 112.8 (d, C-11), 125.4 (d, C-12), 128.7 (s, C-12a), 36.5 (t, C-13), 60.7 (C-13a), 56.5 (q, OCH$_3$), 60.4 (q, OCH$_3$). The said data is corresponding to stepholidine's, so compound 2 is identified as stepholidine.

HPLC analysis of each compound: [Chromatograph condition] instrument: Shimadzu LC 2010A HT Japan); chromatographic column: Xtera (C18, 5 um, 4.6×250 mm); mobile phase: CH$_3$CN-0.025 mol/L KH$_2$PO$_4$ (50:50), adjust with ammonia until pH up to 7; flow rate: 1.0 ml/min; detection wavelength: 225 nm; temperature: 30° C.

TABLE 5

| HPLC analysis of each compound | | | |
|---|---|---|---|
| | Retention time (minute) | | |
| | 8.475 | 5.342 | 4.446 |
| Sequence number of compound | Compound 1 | Compound 2 | Compound 3 |
| Chinese name of compound | (−)四氢巴马丁 | 紫堇达明碱 | 千金藤啶碱 |

TABLE 5-continued

HPLC analysis of each compound

|  | Retention time (minute) | | |
| --- | --- | --- | --- |
|  | 8.475 | 5.342 | 4.446 |
| English name of compound | (−)-Tetrahydropalmatine | (−) Corydalmine | (−) Stepholidine |
| Relative content | 25.130% | 13.366% | 17.623% |

Experiment 4

Research of Total Alkaloids of Radix Stephaniae Epigaeae for Protracted Withdrawal Symptom of Opioids Addiction Experiment Data 119 heroin dependence treatment inpatients, conform to the DSM-IV opioids dependence diagnosis standard, stochastically divide into 3 groups after withdrawal heroin 7d, take 60 mg total alkaloids of Radix Stephaniae Epigaeae or placebo with same appearance twice per day (prepared according to experiment 1 method) respectively, treat for one month, follow-up for two months. Assess protracted withdrawal symptom and psychology craving at day 7, day 14, day 21, day 28, day 35, day 42, day 56, day 70 after admission. There are basically no significant difference between each drug abstainer group at aspects of age, education level, professional condition, age begin to use illegal drug, drug type, drug abuse time per day and so on, and every factors assigned in each group is quite balanced.

Effect of Total Alkaloids of Radix Stephaniae Epigaeae for Overall Protracted Withdrawal Symptom Grade of overall protracted withdrawal symptom decreases more quickly than grades of control group, examine variance homogeneity of two groups, at α=0.05 level, variance of overall protracted withdrawal symptom is homogeneous. Single factor variance analysis (F examination) indicates: grade of total alkaloids of Radix Stephaniae Epigaeae group is lower than the placebo group. There is difference between grade of day 7 after administration and grade of day 5, day 14 after drug withdrawal (P<0.05).

TABLE 6

Total grade changes comparison of total alkaloids of Radix Stephaniae Epigaeae for protracted withdrawal symptom

| Time (day) | Total alkaloids of Radix Stephaniae Epigaeae group (n = 57) | Placebo group (n = 61) | T value | P. |
| --- | --- | --- | --- | --- |
| Abstinence day7 | 41.61 ± 21.80 | 41.72 ± 17.44 | 0.030 | |
| Administration day7 | 31.02 ± 15.64* | 36.64 ± 13.42 | 2.090 | |
| Day 14 | 26.77 ± 12.76 | 29.56 ± 11.81 | 1.230 | |
| Day 21 | 25.75 ± 11.34 | 27.98 ± 10.82 | 1.090 | |
| Day 28 | 24.00 ± 12.05 | 25.26 ± 10.39 | 1.576 | |
| Drug withdrawal day 5 | 17.36 ± 9.43** | 23.71 ± 12.30 | 3.130 | |
| Day 14 | 13.39 ± 9.11* | 17.86 ± 11.22 | 2.366 | |
| Day 28 | 12.10 ± 8.24 | 14.67 ± 6.18 | 1.924 | |

Effect for Body Protracted Withdrawal Symptom

Single factor variance analysis (F examination) indicates: there is no significant difference in every group at admission day, at day 7, day 21, day 28 after administration, at day 5, day 14 after drug withdrawal; there is significant difference (P<0.05) between in every group at day 14 after administration and day 5 after drug withdrawal.

TABLE 7

Curative effects comparison of total alkaloids of Radix Stephaniae Epigaeae for body protracted withdrawal symptom

| Time (day) | Total alkaloids of Radix Stephaniae Epigaeae group (n = 58) | Placebo group (n = 61) | T value | P. |
| --- | --- | --- | --- | --- |
| Abstinence day 7 | 11.12 ± 7.66 | 11.23 ± 6.33 | 0.086 | |
| Administration day 7 | 7.75 ± 5.82 | 8.73 ± 4.88 | 0.994 | |
| Day 14 | 5.48 ± 4.25* | 7.36 ± 4.29 | 2.400 | |
| Day 21 | 5.45 ± 4.55 | 5.53 ± 3.67 | 0.105 | |
| Day 28 | 4.43 ± 4.30 | 5.16 ± 3.73 | 0.991 | |
| Drug withdrawal day 5 | 2.92 ± 3.19* | 4.16 ± 3.60 | 1.985 | |
| Day 14 | 2.45 ± 3.16 | 2.76 ± 3.10 | 0.540 | |
| Day 28 | 1.67 ± 2.65 | 2.56 ± 2.30 | 1.959 | |

*P < 0.05, compare total alkaloids of Radix Stephaniae Epigaeae group with the placebo group Influence for Psychic Dependence—"Craving" Symptom Total alkaloids of Radix Stephaniae Epigaeae have significant influence for psychology craving. Compare with control group, single factor variance analysis (F examination) indicates: there is difference (P<0.05) at day 7, day 14, day 21 after administration, there is significant difference (P<0.01) at day 5, day 14, day 28 after drug withdrawal.

TABLE 8

Curative effects comparison of total alkaloids of Radix Stephaniae Epigaeae for craving symptom

| Time (day) | Total alkaloids of Radix Stephaniae Epigaeae group (n = 58) | Placebo group (n = 61) | T value | P. |
| --- | --- | --- | --- | --- |
| Abstinence day 7 | 12.24 ± 6.07 | 12.48 ± 5.42 | 0.228 | |
| Administration day 7 | 9.10 ± 5.88* | 11.68 ± 4.47 | 2.790 | |
| Day 14 | 7.16 ± 4.31* | 9.20 ± 4.14 | 2.634 | |
| Day 21 | 7.08 ± 4.06* | 9.34 ± 4.01 | 3.054 | |
| Day 28 | 5.64 ± 3.98** | 8.59 ± 3.28 | 4.422 | |
| Drug withdrawal day 5 | 4.75 ± 3.70** | 8.34 ± 5.10 | 4.376 | |
| Day 14 | 3.54 ± 3.30** | 7.43 ± 3.70 | 6.040 | |
| Day 28 | 3.52 ± 2.56** | 7.00 ± 3.46 | 6.211 | |

*P < 0.05, compare total alkaloids of Radix Stephaniae Epigaeae group with the placebo group
**P < 0.01, compare total alkaloids of Radix Stephaniae Epigaeae group with the placebo group With synchronization double blind, random parallel, control design, the said experiments avoid subjective factors as far as possible in order to objectively assess the curative effects of total alkaloids of Radix Stephaniae Epigaeae. The test results show that protracted withdrawal symptom is prolonged, but along with time pasting, it is still gradually weaken, and the speed vary from quick to to slow down, the symptom weaken rather fast at first three weeks before drug withdrawal, then the speed slowed down obviously; and total alkaloids of Radix Stephaniae Epigaeae have effect to overall protracted withdrawal symptom. From every factor aspect of protracted withdrawal symptom, the experiment indicates that total alkaloids of Radix Stephaniae Epigaeae have obvious curative effect to single item symptoms of protracted heroin withdrawal symptom, such as ache, palpitation, anxious and restless, sleeping disorder and so on.

Experiment 5

Penk mRNA Expression Experiment of Total Alkaloids of Radix Stephaniae Epigaeae in Partial Brain Structure of Morphine Dependence Rat In each detected sites, compare with normal control group, Penk mRNA expression of dependence group decrease significantly (P<0.05). At treatment day 12, compare with normal saline group, total alkaloids of Radix Stephaniae Epigaeae group (obtain in experiment 2) except has no significantly increasing Penk mRNA expression in CPu, has significantly increasing Penk mRNA expression in all other detected sites (P<0.05). At day 30 after treatment, compare with normal saline group, total alkaloids of Radix Stephaniae Epigaeae group has significantly increasing Penk mRNA expression in all detected sites (P<0.05).

TABLE 9

Influence for Penk mRNA gene expression of total alkaloids of Radix Stephaniae Epigaeae in related brain sites of morphine dependence rat
($\bar{x} \pm s$, n = 120)

|  | NAc | CPu | PFC | VTA |
|---|---|---|---|---|
| Normal group | 0.202 ± 0.0758 | 0.2103 ± 0.0521 | 0.3214 ± 0.0547 | 0.2990 ± 0.0379 |
| Mor + NS12 | 0.0974 ± 0.0087** | 0.1542 ± 0.0348** | 0.1087 ± 0.0396** | 0.0594 ± 0.0091** |
| Mor + total alkaloids of Radix Stephaniae Epigaeae 12 | 0.1874 ± 0.0481## | 0.1628 ± 0.0763** | 0.3027 ± 0.0703## | 0.1609 ± 0.0494**## |
| Mor + NS30 | 0.1736 ± 0.0695** | 0.1675 ± 0.0829** | 0.2076 ± 0.0708** | 0.0631 ± 0.0078** |
| Mor + total alkaloids of Radix Stephaniae Epigaeae 30 | 0.1946 ± 0.0827 | 0.2031 ± 0.0583## | 0.3158 ± 0.0629## | 0.2973 ± 0.0824## |

**P < 0.01, compare with normal control group
P < 0.01, compare with morphine + normal saline group Experiment 6

Penk mRNA Expression Experiment of Total Alkaloids of Radix Stephaniae Epigaeae in Arcuate Nucleus of Morphine Dependence Rat Compared with normal control group's, Penk mRNA expression in arcuate nucleus of the group given normal saline after morphine dependence decreases significantly (P<0.05), and there is no natural recovery until day 30 after administration, less than control group significantly. At day 12 after treatment, Penk mRNA expression is same to normal saline group, all of them are less than normal control group, at day 30 after continuous treatment, Penk mRNA expression of total alkaloids of Radix Stephaniae Epigaeae group (obtain in experiment 2) significantly increase, and there is significant different compared with normal saline group (P<0.05); but there is no different to normal control group.

Through the said experiment of total alkaloids of Radix Stephaniae Epigaeae influent treatment, it indicates that: except inhibit $D_2R$ mRNA gene expression in nucleus accumbens, Penk mRNA in ventral tegmental area and caudate-putamen nucleus, POMC mRNA in arcuate nucleus, is less than control group at day 12, recover to normal at day 30; $D_1R$ mRNA gene expression in other ventral tegmental area (VTA), amygdaloid nucleus (AMY), caudate-putamen nucleus (CPU) and prefrontal cortex (PFC), $D_2R$ mRNA gene expression in ventral tegmental area, caudate-putamen nucleus are significantly more than normal saline group's not only at day 12 but also at day 30 after administration, and there is no different to normal control group.

The said experiment indicates: total alkaloids of Radix Stephaniae Epigaeae have significant reverse effect to TH increase and DAmRNA decrease after drug addiction withdrawal. It avoid excessive TH immunity positive reaction, decrease the inhibition of $D_1R$ mRNA and $D_2R$ mRNA gene expression in related brain area, and accelerate EOP, DA nervous system function naturally recover course in back brain after morphine addiction withdrawal. It gives a important basis for using the said invention medicine to treat opioids addiction.

Experiment 7

Influence Experiment of the Said Pharmaceutical Composition Tablet for Rat Self-Administration Behavior Experimental medicine: the said pharmaceutical composition tablet (obtain in experiment 1); model medication; morphine hydrochloride produced by Qinghai pharmaceutical manufacture limited company. Surgery anaesthetic: Pentobarbitol sodium. Conventional antibiotic: Penicillin G Animal: SD rats, 280 g-350 g, male, second degree.

Self-administration experimental apparatus: rat self-administration experimental apparatus is invented by Beijing University drug dependence institute, and it include two big basic systems comprising a self-administration system and a control system. The series of equipment are compose of industrial control computer, self-administration data collect and control system, special self-administration cage, constant speed infusion pump, intravenous infusion pipe system (including air filter, countercurrent prevent valve, shaft and so on), fluid road protect pipe, vest and so on.

Administration route: administration model with morphine hydrochloride by iv, divide to 3 groups according to dosage: 1.0 mg·kg$^{-1}$/INJ (MAX=50), 0.5 mg·kg$^{-1}$/INJ (MAX=100), 2.0 mg·kg$^{-1}$/INJ (MAX=50); convalescence medication by ig route, simulate clinic administration route. 8 rats in control group (NS1-NS8): ig normal saline, 1 ml/rat, Bid, GYA group 8rats (GYA1-GYA8): ig starting material extract solution of the said pharmaceutical composition tablet, 5.25 mg·kg$^{-1}$, Bid, GYB group 8 rats (GYB1-GYB8): ig starting material extract solution of the said pharmaceutical composition tablet, 5.25 mg·kg$^{-1}$, Bid.

Experiment results of establishment and comparison for self-administration model: success symbol of self-administration model is animal-forming initiative drug seeking behavior response (touch nose switch) to express its craving to obtain drug. The response number and drug dosage of experimental animals are very unstable. In this experiment, training experimental animals for about ten times, rats will establish inject drug conditioned reflex through average 5-7 days training (average 5 days). Then, strengthen effect of morphine will make rats initiatively seek and touch nose switch to gain drug injection. When it became stable self-administration behavior, self-administration behavior times of 22 rats are no significant different.

TABLE 10

Mean comparison of self-administration behavior number before the treatment (n = 22)

| Animal number (n = 22) | Control group (n = 8) | GYA group (n = 8) | GYB group (n = 6) |
|---|---|---|---|
| $N_1$ | 47.25 | 44.67 | 45.20 |
| $N_2$ | 47.00 | 45.50 | 39.25 |
| $N_3$ | 50.80 | 44.60 | 49.20 |
| $N_4$ | 50.80 | 25.50 | 43.50 |
| $N_5$ | 47.60 | 41.50 | 49.40 |
| $N_6$ | 48.60 | 44.25 | 51.00 |
| $N_7$ | 45.60 | 44.25 | — |
| $N_8$ | 45.20 | 44.00 | — |
| Mean | 47.86 | 41.78 | 46.26 |

Influence for Rat Self-Administration Response Number Pre-Administration and Post-Administration of the Said Pharmaceutical Composition Tablet Take rats have established stable self-administration behavior, treat with extract solution of The said pharmaceutical composition tablet crude drugs respectively, or reuse after control treatment with normal saline for a month, come back to former administration correlation environment, produced corresponding stress response, control group and GYA group are gradually recover self-administration (morphine) response. Control group recover rather quick, sensitive rats recover to the level before administration at 3d, average 5d; response number of GYA group is lower than control group, average 8d; there is no different between 2 groups after 8 days. We change the administration route at GYB group, inject 5.25 mg·kg$^1$ ig continuously after reuse with extract solution of the said pharmaceutical composition tablet crude drugs, one time per day, then self-administration behavior is completely inhibited.

TABLE 11

Response number of each group at relapse phase ($\bar{x} \pm s$, n = 22)

| Relapse day n | Control group (n = 8) | GYA group (n = 8) | GYB group (n = 6) |
|---|---|---|---|
| Day 1 | 2.38 ± 2.27 | 1.00 ± 1.42** | 0.67 ± 1.03** |
| Day 2 | 8.63 ± 6.68 | 4.13 ± 3.88** | 0.33 ± 0.82** |
| Day 3 | 11.75 ± 13.52 | 6.25 ± 5.45** | 2.50 ± 1.76** |
| Day 4 | 26.13 ± 16.32 | 8.88 ± 7.43** | 2.50 ± 2.07** |
| Day 5 | 39.75 ± 13.52 | 16.00 ± 6.30** | 1.50 ± 1.38** |
| Day 6 | 50.00 ± 2.14 | 22.00 ± 13.87** | 1.17 ± 1.94** |
| Day 7 | 48.86 ± 3.32 | 35.00 ± 13.28* | 2.67 ± 2.34** |
| Day 8 | 40.75 ± 14.48 | 43.00 ± 8.67 | 3.33 ± 4.37** |

Note:
Compare with control group: *p < 0.05 **p < 0.01/p < 0.001

TABLE 12

Influence for pre-administration and post-administration rat self-administration response number of the said pharmaceutical composition tablet (n = 22)

| Animal number | Response time (5 days before the treatment) Mean | Day 1 | Day 2 | Day 3 | Day 4 | Day 5 | Day 6 | Day 7 | Day 8 |
|---|---|---|---|---|---|---|---|---|---|
| NS1 | 47.25 | 2 | 25 | 41 | 51 | 51 | 51 | 51 | 51 |
| NS2 | 47.00 | 1 | 10 | 15 | 22 | 51 | 51 | 51 | 51 |
| NS3 | 50.80 | 5 | 4 | 1 | 13 | 22 | 45 | 47 | 34 |
| NS4 | 50.80 | 0 | 5 | 1 | 10 | 42 | 51 | 51 | 51 |
| NS5 | 47.60 | 5 | 7 | 15 | 51 | 51 | 51 | 51 | 50 |
| NS6 | 48.60 | 1 | 10 | 15 | 28 | 51 | 51 | 51 | 44 |
| NS7 | 45.60 | 5 | 4 | 1 | 15 | 22 | 49 | 47 | 34 |
| NS8 | 45.20 | 0 | 5 | 5 | 19 | 28 | 51 | 42 | 51 |
| $\bar{x} \pm s$ | 47.86 | 2.38 ± 2.27** | 8.75 ± 6.68** | 11.75 ± 13.52** | 26.13 ± 16.32** | 39.75 ± 13.52 | 50.00 ± 2.14 | 48.86 ± 3.32 | 40.75 ± 14.48 |
| GYA1 | 44.67 | 0 | 1 | 2 | 5 | 12 | 7 | 21 | 30 |
| GYA2 | 45.50 | 0 | 1 | 3 | 5 | 7 | 7 | 25 | 35 |
| GYA3 | 44.60 | 0 | 0 | 1 | 1 | 15 | 17 | 27 | 34 |
| GYA4 | 25.50 | 2 | 6 | 8 | 24 | 19 | 26 | 19 | 47 |
| GYA5 | 41.50 | 1 | 5 | 4 | 4 | 11 | 23 | 52 | 45 |
| GYA6 | 44.25 | 0 | 3 | 17 | 13 | 21 | 25 | 43 | 51 |
| GYA7 | 44.25 | 4 | 12 | 11 | 6 | 16 | 20 | 47 | 51 |
| GYA8 | 44.00 | 1 | 5 | 4 | 13 | 27 | 51 | 46 | 51 |
| $\bar{x} \pm s$ | 41.78 | 1.00 ± 1.42**## | 4.125 ± 3.88**## | 6.25 ± 5.45**## | 8.88 ± 7.43**## | 16.00 ± 6.30**## | 22.00 ± 13.87*## | 35.00 ± 13.28# | 43.00 ± 8.67 |
| GYB1 | 45.20 | 2 | 0 | 3 | 0 | 1 | 0 | 2 | 1 |
| GYB2 | 39.25 | 2 | 0 | 0 | 1 | 1 | 0 | 0 | 0 |
| GYB3 | 49.20 | 0 | 0 | 3 | 2 | 2 | 0 | 5 | 11 |
| GYB4 | 43.50 | 0 | 2 | 1 | 3 | 0 | 1 | 4 | 0 |
| GYB5 | 49.40 | 0 | 0 | 3 | 6 | 4 | 5 | 0 | 2 |
| GYB6 | 51.00 | 0 | 0 | 3 | 5 | 1 | 1 | 5 | 6 |
| $\bar{x} \pm s$ | 46.26 | 0.67 ± 1.03**## | 0.33 ± 0.82**## | 2.50 ± 1.76**## | 2.50 ± 2.07**## | 1.50 ± 1.38**## | 1.17 ± 1.94**## | 1.67 ± 2.34**## | 3.33 ± 4.37**## |

Note:
Compare with pre-treatment: *p < 0.05 **p < 0.01/p < 0.001
Compare with control group: #p < 0.05 ##p < 0.01/p < 0.001

Influence for Pre-Administration TDD of the Said Pharmaceutical Composition Tablet After establishment of self-administration model, TDD is relatively stable, the rats will initiatively seek nose switch to gain morphine injection. Rising each inject dosage (2 mg·kg-1/INJ), the response number of touch nose switch decreases correspondingly. Reducing each inject dosage (0.5 mg·kg-1/INJ), the response number of touch nose switch increases correspondingly. Keeping morphine dosage unchanged, self-administration TDD is no different in 3 groups before the treatment.

administration (morphine) behavior gradually. It quickly recovers TDD of normal saline group, and recovers to the pre-administration level for average 3 days. TDD of Guiyuan A group is lower than synchronization control, recover to the pre-administration level after average 8 days.

Continuous administration after reusing Guiyuan group B, and it not recover TDD at last, forgot former custom self-administration behavior, without reaction to administration environment and signal, not seek to touch nose switch at all. Compare with control group, the said pharmaceutical composition tablet has significant curative effect to TDD at relapse phase ($p<0.001$).

TABLE 14

Influence for TDD of the said pharmaceutical composition tablet at pre-administration and post-administration

| Animal number | TDD (pre-treatment) Before 5 days ($\bar{x}$) | TDD (post-treatment) | | | | | | | |
|---|---|---|---|---|---|---|---|---|---|
| | | Day 1 | Day 2 | Day 3 | Day 4 | Day 5 | Day 6 | Day 7 | Day 8 |
| $NS_1$ | 14.96 | 0.74 | 8.88 | 15.17 | 18.87 | 18.87 | 18.26 | 18.26 | 18.26 |
| $NS_2$ | 19.58 | 0.37 | 3.68 | 5.52 | 8.09 | 16.63 | 16.63 | 16.63 | 16.63 |
| $NS_3$ | 13.148 | 1.63 | 1.30 | 0.33 | 4.24 | 7.17 | 14.67 | 15.32 | 11.08 |
| $NS_4$ | 11.91 | 0.00 | 1.66 | 0.34 | 3.37 | 15.46 | 18.77 | 18.77 | 18.77 |
| $NS_5$ | 14.66 | 1.86 | 2.60 | 5.58 | 18.97 | 18.97 | 18.67 | 18.67 | 3.66 |
| $NS_6$ | 11.36 | 0.37 | 3.68 | 5.52 | 10.30 | 18.77 | 18.77 | 16.93 | 14.61 |
| $NS_7$ | 12.51 | 1.63 | 1.30 | 0.33 | 4.89 | 7.17 | 15.97 | 15.32 | 11.08 |
| $NS_8$ | 12.32 | 0.00 | 1.69 | 1.69 | 6.40 | 10.30 | 18.77 | 15.46 | 18.77 |
| $\bar{x}$ | 13.71 | 0.82** | 3.10** | 4.31** | 9.39* | 14.19* | 17.56* | 16.92* | 14.11* |
| $GY_{A1}$ | 14.49 | 0.00 | 0.36 | 0.72 | 1.79 | 4.30 | 2.51 | 7.52 | 10.56 |
| $GY_{A2}$ | 12.43 | 0.00 | 0.37 | 1.10 | 1.84 | 2.58 | 2.58 | 9.20 | 12.88 |
| $GY_{A3}$ | 13.16 | 0.00 | 0.00 | 0.36 | 0.36 | 5.33 | 6.04 | 9.59 | 12.07 |
| $GY_{A4}$ | 11.53 | 0.69 | 2.07 | 2.76 | 8.28 | 6.56 | 8.97 | 6.56 | 16.22 |
| $GY_{A5}$ | 8.72 | 0.33 | 1.66 | 1.33 | 1.33 | 3.65 | 7.64 | 16.12 | 13.95 |
| $GY_{A6}$ | 18.18 | 0.00 | 1.16 | 6.55 | 5.01 | 8.09 | 9.63 | 16.56 | 18.72 |
| $GY_{A7}$ | 18.96 | 1.61 | 4.82 | 4.42 | 2.41 | 6.43 | 8.04 | 18.90 | 20.50 |
| $GY_{A8}$ | 17.83 | 0.40 | 1.99 | 1.59 | 5.16 | 10.72 | 20.25 | 18.26 | 20.25 |
| $\bar{x}$ | 14.41 | 0.38**$^{\#\#}$ | 1.56**$^{\#}$ | 2.35**$^{\#}$ | 3.27**$^{\#}$ | 5.96**$^{\#\#}$ | 8.20*$^{\#}$ | 12.84*$^{\#}$ | 15.64*$^{\#}$ |
| $GY_{B1}$ | 12.21 | 0.76 | — | 1.01 | 0.00 | 0.34 | — | 0.58 | 0.29 |
| $GY_{B2}$ | 8.18 | 0.70 | — | — | 0.35 | 0.35 | — | — | — |
| $GY_{B3}$ | 17.79 | — | — | 1.22 | 0.81 | 0.81 | — | 2.03 | 4.46 |
| $GY_{B4}$ | 14.30 | — | 0.80 | 0.40 | 1.19 | — | 0.39 | 1.60 | — |
| $GY_{B5}$ | 15.20 | — | — | 1.23 | 2.46 | 1.64 | 2.05 | — | 0.82 |
| $GY_{B6}$ | 17.99 | — | — | 1.90 | 1.14 | 0.38 | 0.38 | 1.90 | 2.28 |
| $\bar{x}$ | 14.28 | 0.24**$^{\#\#}$ | 0.13**$^{\#}$ | 0.96**$^{\#\#}$ | 0.99**$^{\#\#}$ | 0.57**$^{\#\#}$ | 0.47**$^{\#\#}$ | 1.02**$^{\#\#}$ | 1.31**$^{\#\#}$ |

Note:
Compare with pre-treatment: *$p < 0.05$ **$p < 0.01$/$p < 0.001$

TABLE 13

Mean comparison of pre-treatment self-administration TDD (n = 22)

| Animal number | Control group (n = 8) | GYA group (n = 8) | GYB group (n = 6) |
|---|---|---|---|
| N1 | 14.96 | 14.49 | 12.21 |
| N2 | 19.58 | 12.43 | 8.18 |
| N3 | 13.14 | 13.16 | 17.79 |
| N4 | 11.91 | 11.53 | 14.30 |
| N5 | 14.66 | 8.72 | 15.20 |
| N6 | 11.36 | 18.18 | 17.99 |
| N7 | 12.51 | 18.96 | — |
| N8 | 12.32 | 17.83 | — |
| Mean | 13.71 | 14.41 | 14.28 |

Influence for TDD of the Said Pharmaceutical Composition Tablet at Relapse Phase When the rats return to cage, the environment induces TDD. Normal saline group and Guiyuan A group can recover self-

TABLE 15

TDD Comparison of the said pharmaceutical composition tablet among groups at relapse phase ($\bar{x} \pm s$)

| Relapse day n | Control group (n = 8) | $GY_A$ group (n = 8) | $GY_B$ group (n = 6) |
|---|---|---|---|
| Day 1 | 2.05 ± 3.73 | 0.38 ± 0.56*** | 0.24 ± 0.38*** |
| Day 2 | 4.26 ± 3.47 | 1.55 ± 1.54*** | 0.13 ± 0.33*** |
| Day 3 | 5.45 ± 5.98 | 2.35 ± 2.13*** | 0.96 ± 0.67*** |
| Day 4 | 8.96 ± 5.89 | 3.27 ± 2.64*** | 0.99 ± 0.85*** |
| Day 5 | 11.41 ± 6.44 | 5.96 ± 2.61*** | 0.59 ± 0.58*** |
| Day 6 | 14.80 ± 6.62 | 8.20 ± 5.57*** | 0.47 ± 0.80*** |
| Day 7 | 14.35 ± 6.36 | 12.84 ± 5.10* | 1.02 ± 0.94*** |
| Day 8 | 14.98 ± 5.12 | 15.64 ± 3.85 | 1.31 ± 1.76*** |

Note:
Compare with control group: *$p < 0.05$ ***$p < 0.001$

Under environment inducing condition, when they returned to the cage (drug addiction environment), saline control group rats completely without body withdrawal symptom recover intravenous self-administration behavior at that day. Compare with that, frequency and response number of rats, which are treated with the said pharmaceutical composition tablet for a month at convalescence stage, all reduced, and they relapse after average 8 days. However, after return to to administration cage, treatment group rats, which take the said pharmaceutical composition tablet once per day, have inhibited intravenous self-administration behavior. It indicates that the said pharmaceutical composition preparation has intervention effect to intravenous self-administration relapse behavior of morphine addiction rats induced by environment.

Experiment 8

Curative Effect Comparison Research of the Pharmaceutical Composition Tablet and Total Alkaloid of Radix Stephaniae Epigaeae (Single-Agent of Radix Stephaniae Epigaeae) for Protracted Withdrawal Symptom Research object: after forced drug addiction treatment for abstinence because of injecting or addicting heroin and other narcotics, the heroin dependence addicts take this invention pharmaceutical composition tablet (obtained in the said invention experiment 1) voluntarily. 26 admission testees are stochastically divided to "this invention pharmaceutical composition compound" group (11 testees), "Radix Stephaniae Epigaeae Single-agent" group (9 testees) and "blank control" group (6 patients). All admission testees accord to DSM-IV pharmaceutical dependence diagnosis standard and opioids withdrawal response diagnosis standard, except various dysphrenia and other serious body diseases. All admission testees take "6.26" drug abstinence capsule (this institute research a preparation containing opioid) for 4-7 days as drug abstinence treatment (all drug withdrawal), but there exists still a part of acute residual withdrawal symptom and slow protracted withdrawal symptom. General condition and group condition of testees are showed as follows. Age, accumulated drug abuse time among 3 testee groups exist no statistics difference (P>0.05), but at drug abuse amount per day, admission body weight, there exists statistics difference because of sampling error factor (P<0.05).

Medicine, assessment standard, assessment content, assessment method and admission standard Administration method and dosage: withdrawal symptom and not appear obvious poison response is a principle. Medications of two research groups are different, give compound group capsule, give single agent group same dosage of compound group's medication, give control group no medicine, give three groups one capsule each time, tid, administration for 10 days.

Assessment standard: assess by 《Withdrawal symptom observation assessment scale》, 《Treatment emergent symptom scale (TESS)》 and 《HAMA anxious assessment scale》 approved by State Drugs Administration, at the same time, assess refer to 《Heroin protracted withdrawal symptom assessment scale》 of Chinese drug dependence institute.

Assessment content: according to research plan request, record truthfully: research medical record briefly; 《Withdrawal symptom observation assessment scale》, Treatment emergent symptom scale (TESS), HAMA anxious assessment scale》, 《Heroin protracted withdrawal symptom assessment scale》, Urine morphine test (TLC); blood routine test, urine routine test; liver and renal function test.

Assessment method: grade according to 《withdrawal symptom observation assessment scale》 and 《Treatment emergent symptom scale (TESS)》 at P.M. 7-8 in every day, determine and record blood pressure, pulse rate and body weight simultaneously. Assess by 《HAMA anxious assessment scale》 once per 5 days. Carry on urine morphine test, blood routine test, urine routine test at pre-admission and post-treatment respectively. All testees are managed with management pattern and regulation in forced drug addiction Rehabilitation. In treatment observation period, the testees participated in morning exercise, study, formation train, entertainment and labor as usual, without any special treatment compared with the other drug abstinents.

Admission standard: stop use other drug abstinence medicines; almost eliminate the acute withdrawal symptom, but still leave certain degree withdrawal symptom. Escape standard: the testees whose urine morphine test is positive after treatment; the testees whose test results are abnormal or who cannot persist the treatment because of body disease after treatment beginning; the testees who escape treatment not because of treatment reason (for example criminal case); the testees refuse to take the medicine after invalid persuade. Comparison of three testee groups for withdrawal symptom grade per day during administration

TABLE 16

General test condition table ($\bar{x} \pm s$)

| | Single-agent group of Radix Stephaniae Epigaeae | | Compound group of the said invention pharmaceutical composition Case number | | Control group | | |
|---|---|---|---|---|---|---|---|
| | n = 11 | | n = 9 | | n = 6 | | |
| | Male 6 | Female 5 | Male 6 | Female 3 | Male 4 | Female 2 | P value |
| Intravenous drug abuse ratio | 8/11 (72.7%) | | 6/9 (66.7%) | | 4/6 (66.7%) | | |
| Age (year) | 22.55 ± 4.75 | | 25.18 ± 6.78 | | 31.33 ± 7.26 | | All > 0.05 |
| Accumulated drug abuse time (month) | 39.45 ± 30.85 | | 32.67 ± 34.96 | | 57.33 ± 45.16 | | All > 0.05 |
| Drug abuse amount per day (g) | 0.80 ± 0.42 | | 0.86 ± 0.12 | | 0.80 ± 0.32 | | All > 0.05 |
| Admission body weight (kg) | 50.05 ± 6.32 | | 59.44 ± 7.29 | | 52.50 ± 9.36 | | All > 0.05 |

TABLE 17

Grade mean per day table of three groups for acute residual withdrawal symptom ($\bar{x} \pm s$)

| Course (day) | Single-agent group of Radix Stephaniae Epigaeae n = 11 | Compound group of the said invention pharmaceutical composition n = 9 | Control group n = 6 | P value |
| --- | --- | --- | --- | --- |
| Day 0 | 9.73 ± 2.57 | 6.78 ± 2.22 | 11.50 ± 4.04 | P1-0 > 0.05 Others < 0.05 |
| Day 1 | 7.36 ± 3.72 | 5.78 ± 3.11 | 9.50 ± 2.95 | P0-3 < 0.05 Others > 0.05 |
| Day 2 | 6.82 ± 2.82 | 4.44 ± 2.65 | 9.00 ± 3.63 | P0-3 < 0.05 Others > 0.05 |
| Day 3 | 6.36 ± 2.38 | 3.33 ± 1.73 | 7.67 ± 3.78 | P1-0 > 0.05 Others < 0.05 |
| Day 4 | 5.73 ± 2.37 | 3.22 ± 1.79 | 5.50 ± 2.43 | P1-3 > 0.05 Others < 0.05 |
| Day 5 | 5.18 ± 2.14 | 3.00 ± 1.58 | 4.67 ± 2.07 | P1-3 > 0.05 Others < 0.05 |
| Day 6 | 4.82 ± 2.93 | 3.00 ± 1.87 | 5.17 ± 2.48 | All > 0.05 |
| Day 7 | 4.09 ± 2.70 | 2.44 ± 2.30 | 4.17 ± 2.14 | All > 0.05 |
| Day 8 | 3.82 ± 2.68 | 3.33 ± 2.29 | 4.33 ± 1.75 | All > 0.05 |
| Day 9 | 4.09 ± 3.02 | 2.56 ± 1.74 | 4.83 ± 2.40 | All > 0.05 |
| Day 10 | 3.02 ± 2.39 | 1.67 ± 1.80 | 2.83 ± 1.94 | All > 0.05 |

With comparison of single-agent group of Radix Stephaniae Epigaeae and compound group of the said invention pharmaceutical composition between u) control group, it indicates that post-administration control or release residual overall withdrawal symptom during drug addiction treatment has following characteristic: withdrawal symptom grade obviously decreases at day 4 during administration, there exists significant different effect (P<0.05), but single-agent group of Radix Stephaniae Epigaeae has no significant different compared with control group (P>0.05). Withdrawal symptom is controlled stably, and it decreases gradually without bounce phenomenon of withdrawal symptom. Grade comparison of drug withdrawal of two test groups

TABLE 18

Mean table for drug withdrawal of two test groups ($\bar{x} \pm s$)

| Course (day) | Single-agent group of Radix Stephaniae Epigaeae n = 11 | Compound group of the said invention pharmaceutical composition n = 9 | P value |
| --- | --- | --- | --- |
| Day 11 | 3.73 ± 2.65 | 1.89 ± 1.62 | >0.05 |
| Day 12 | 3.00 ± 2.86 | 1.33 ± 1.50 | >0.05 |
| Day 13 | 1.82 ± 1.25 | 0.89 ± 0.93 | >0.05 |
| Day 14 | 2.55 ± 12.70 | 1.22 ± 1.39 | >0.05 |
| Day 15 | 1.91 ± 12.70 | 0.67 ± 0.87 | >0.05 |
| Day 16 | 2.18 ± 2.27 | 0.67 ± 1.12 | >0.05 |
| Day 17 | 1.73 ± 1.68 | 0.44 ± 0.88 | >0.05 |
| Day 18 | 0.63 ± 1.20 | 0.11 ± 0.33 | >0.05 |
| Day 19 | 0.46 ± 1.04 | 0.11 ± 0.33 | >0.05 |
| Day 20 | 0.27 ± 0.91 | 0.00 ± 0.00 | >0.05 |

Grades of two test groups have no bounce phenomenon for withdrawal symptom after drug withdrawal, they all decrease gradually day by day, and there is no significant different between two groups (P>0.05).

Comparison of Two Testee Groups for Average Sleeping Time Pre Day after Administration At day 9,10 after administration, sleeping time induced by the said invention pharmaceutical composition compound is longer than Radix Stephaniae Epigaeae single-agent and control group (P<0.05); except above, there is no significant different between other days (P>0.05). (Note: During administration, wake testees up to keep watch can influent the observation.)

TABLE 19

Mean table of three groups for sleeping time in evening ($\bar{x} \pm s$)

| Course (day) | Single-agent group of Radix Stephaniae Epigaeae n = 11 | Compound group of the said invention pharmaceutical composition n = 9 | Control group n = 6 | P value |
| --- | --- | --- | --- | --- |
| Day 0 | 1.09 ± 1.02 | 2.56 ± 1.74 | 1.17 ± 1.17 | P1-3 < 0.05 others > 0.05 |
| Day 1 | 2.75 ± 2.25 | 4.22 ± 2.54 | 2.27 ± 2.49 | All > 0.05 |
| Day 2 | 3.36 ± 2.16 | 4.11 ± 2.76 | 1.92 ± 1.02 | All > 0.05 |
| Day 3 | 3.64 ± 2.11 | 3.22 ± 2.99 | 2.75 ± 1.84 | All > 0.05 |
| Day 4 | 3.55 ± 1.75 | 5.00 ± 2.69 | 3.42 ± 0.92 | All > 0.05 |
| Day 5 | 4.18 ± 1.94 | 4.56 ± 1.74 | 3.58 ± 2.01 | All > 0.05 |
| Day 6 | 3.73 ± 1.95 | 4.00 ± 2.24 | 2.75 ± 0.88 | All > 0.05 |
| Day 7 | 3.82 ± 2.27 | 4.22 ± 2.49 | 2.08 ± 1.28 | All > 0.05 |
| Day 8 | 4.27 ± 1.62 | 4.78 ± 1.72 | 3.17 ± 1.47 | All > 0.05 |
| Day 9 | 4.91 ± 1.30 | 5.56 ± 1.51 | 3.50 ± 1.38 | P1-0 > 0.05 < 0.05 |
| Day 10 | 4.82 ± 2.27 | 5.44 ± 1.51 | 3.45 ± 1.41 | P1-0 > 0.05 < 0.05 |

Grade Mean Comparison of Adverse Reaction

Adverse reaction grade of the said invention pharmaceutical composition compound is obviously lower than Radix Stephaniae Epigaeae single-agent, and there is significant different (P<0.05).

TABLE 20

Grade mean table of two groups for adverse reaction per day

| Course (day) | Single-agent group of Radix Stephaniae Epigaeae n = 11 | Compound group of the said invention pharmaceutical composition n = 9 | P value |
|---|---|---|---|
| Day 1 | 5.55 ± 2.07 | 4.32 ± 1.16 | >0.05 |
| Day 2 | 5.09 ± 1.22 | 3.65 ± 1.16 | <0.05 |
| Day 3 | 5.09 ± 2.30 | 3.44 ± 1.34 | >0.05 |
| Day 4 | 4.91 ± 2.39 | 4.42 ± 2.17 | >0.05 |
| Day 5 | 5.55 ± 2.34 | 3.44 ± 1.34 | <0.05 |
| Day 6 | 5.00 ± 2.37 | 4.10 ± 0.88 | >0.05 |
| Day 7 | 4.73 ± 2.65 | 3.87 ± 1.00 | >0.05 |
| Day 8 | 3.73 ± 1.85 | 3.64 ± 1.16 | >0.05 |
| Day 9 | 4.55 ± 1.75 | 3.65 ± 1.06 | >0.05 |
| Day 10 | 4.00 ± 1.84 | 2.88 ± 1.73 | >0.05 |

Through above experiment, it was indicated that Radix Stephaniae Epigaeae single-agent and the said invention pharmaceutical composition compound can both control acute residual withdrawal symptom after heroin dependence treatment, but its symptom control effect of the said invention pharmaceutical composition compound is better than effect of Radix Stephaniae Epigaeae single-agent; adverse reaction of compound is less than Radix Stephaniae Epigaeae single-agent, the compound has no obviously poisonous effect and side effect, and is safer and more reliable; the testees are rather accept to this medicine well, and also without dependence.

Experiment 9

Screen for Raw Materials of Pharmaceutical Composition and Comparison Research of Clinic Curative Effect Medicine, Assessment Standard, Assessment Content, Assessment Method and Admission Standard Medicine:

Starting material A: Radix Ginseng 500 g, Rhizoma Corydalis 1600 g, Radix Astragali 2500 g, Radix Angelicae Sinensis 500 g, Radix Ophiopogonis 600 g; capsule 0.4 g/capsule, 2-3 capsules/time 3 times/day.

Starting material B: Radix Ginseng 500 g, Radix Stephaniae Japonicae 1600 g, Radix Astragali 2500 g, Radix Angelicae Sinensis 500 g, Radix Ophiopogonis 600 g; capsule 0.4 g/capsule, 2-3 capsules/time 3 times/day.

Starting material C: Radix Ginseng 500 g, Caulis Fibraureae 1600 g, Radix Astragali 2500 g, Radix Angelicae Sinensis 500 g, Radix Ophiopogonis 600 g; capsule 0.4 g/capsule, 2-3 capsules/time 3 times/day.

Starting material D: Radix Ginseng 300 g, Radix Stephaniae Epigaeae 1600 g, Radix Astragali 1000 g, Radix Angelicae Sinensis 500 g, Radix Ophiopogonis 300 g; capsule 0.35 g/capsule, 2-3 capsules/time 3 times/day.

Starting material E: total alkaloid of Radix Stephaniae Epigaeae (obtain by experiment 2). Tablet 0.35 g 2-3 tablets/time 3 times/day.

Placebo: fill capsule with equal weight pharmaceutical starch: 2-3 capsules/time, 3 times/day. tid, administration 10 day.

Assessment index: assess clinic assessment of new drug abstain medicine by 《clinic research assessment rule of new drug abstain medicine》 issued by State Drugs Administration. Assessment index includes: 《Withdrawal symptom observation assessment scale》, 《Treatment emergent symptom scale (TESS)》, 《HAMA anxious assessment scale》, at the same time, assess refer to 《Heroin protracted withdrawal symptom assessment scale》 of Chinese drug dependence institute.

Grade standard: I. serious degree: 0=no symptom, 1=mild, post-inquiry symptom; 2=moderate, initiative states symptom, endurable, 3=serious symptom, unendurable: II. Relation to administration: 0=irrelevant, 1=possible relevant, 2=quite possible relevant, 3=affirmably relevant.

Assessment method: grade according to 《Withdrawal symptom observation assessment scale》 and 《Treatment emergent symptom scale (TESS)》 at P.M. 10 in every day, determine and record blood pressure, pulse rate and body weight simultaneously. Assess by 《HAMA anxious assessment scale》 once per 5 days. Carry on urine morphine test, blood routine test, urine routine test at pre-admission and post-treatment respectively.

Admission standard and escape standard: stop use heroines narcotics and methadone, buprenorphine and so on of opioids drug abstinence medicines; almost eliminate the acute withdrawal symptom, but still leave certain degree withdrawal symptom. The testees whose urine morphine test is positive after treatment; the testees whose test results are abnormal or who cannot persist the treatment because of body disease after treatment beginning; the testees who escape treatment not because of treatment reason (for example criminal case); the testees refuse to take the medicine after invalid persuade.

Result of Each Group Control Protracted Withdrawal Symptom of Drug Addiction Treatment Effect All testees are treated according to administration project and course designed before experiment, and each group smoothly completes the treatment course.

TABLE 21

Testee grade mean per day table of each group for protracted withdrawal symptom

| Course (Day) | Group A N = 15 X̄ ± SD | Group B N = 15 X̄ ± SD | Group C N = 15 X̄ ± SD | Group D N = 20 X̄ ± SD | Group E N = 15 X̄ ± SD | Control group N = 18 X̄ ± SD |
|---|---|---|---|---|---|---|
| 0 | 14.73 ± 2.57 | 13.73 ± 2.24 | 14.73 ± 2.27 | 15.25 ± 2.22 | 14.73 ± 2.57 | 14.50 ± 4.04 |
| 1 | 12.87 ± 3.72 | 12.36 ± 3.32 | 12.36 ± 3.12 | 11.78 ± 3.11 | 12.36 ± 3.72 | 13.50 ± 2.95 |
| 2 | 11.20 ± 2.22 | 11.35 ± 2.42 | 10.02 ± 2.23 | 9.44 ± 2.65 | 10.82 ± 2.82 | 12.00 ± 3.63 |
| 3 | 9.14 ± 2.31 | 10.21 ± 2.58 | 10.15 ± 2.58 | 8.33 ± 1.73 | 8.36 ± 2.38 | 10.67 ± 3.78 |
| 4 | 8.56 ± 2.27 | 9.73 ± 2.33 | 9.73 ± 2.24 | 6.22 ± 1.79 | 6.73 ± 2.37 | 10.12 ± 2.43 |

TABLE 21-continued

Testee grade mean per day table of each group for protracted withdrawal symptom

| Course (Day) | Group A N = 15 $\bar{X} \pm SD$ | Group B N = 15 $\bar{X} \pm SD$ | Group C N = 15 $\bar{X} \pm SD$ | Group D N = 20 $\bar{X} \pm SD$ | Group E N = 15 $\bar{X} \pm SD$ | Control group N = 18 $\bar{X} \pm SD$ |
|---|---|---|---|---|---|---|
| 5 | 7.20 ± 2.17 | 8.35 ± 2.22 | 7.14 ± 2.82 | 5.00 ± 1.58 | 5.18 ± 2.14 | 9.67 ± 2.07 |
| 6 | 6.36 ± 2.63 | 6.27 ± 2.63 | 5.32 ± 2.13 | 3.00 ± 1.87 | 4.82 ± 2.93 | 8.17 ± 2.48 |
| 7 | 6.12 ± 2.40 | 5.22 ± 2.60 | 4.13 ± 2.72 | 2.44 ± 2.30 | 4.09 ± 2.70 | 6.17 ± 2.14 |
| 8 | 5.80 ± 2.58 | 4.80 ± 2.28 | 4.24 ± 2.66 | 3.33 ± 2.29 | 4.12 ± 2.68 | 6.33 ± 1.75 |
| 9 | 4.26 ± 3.12 | 4.26 ± 3.02 | 4.12 ± 3.07 | 2.56 ± 1.74 | 3.09 ± 3.02 | 5.83 ± 2.40 |
| 10 | 4.16 ± 3.07 | 3.82 ± 2.39 | 3.02 ± 2.25 | 1.67 ± 1.80 | 2.23 ± 2.39 | 5.23 ± 1.94 |

Grade testees per day of each group during administration, compare with control group, residual withdrawal symptom of each administration group was controlled or released, total grades decrease gradually without bounce phenomenon. The curative effect order is group D, group E, group C, group B and group A, wherein withdrawal symptom total grade of group D decreases faster than other groups, and effect of group A is poor.

TABLE 22

Total testee grade comparison of each group for HAMA anxious amount

| Course (Day) | Group A N = 15 $\bar{X} \pm SD$ | Group B N = 15 $\bar{X} \pm SD$ | Group C N = 15 $\bar{X} \pm SD$ | Group D N = 20 $\bar{X} \pm SD$ | Group E N = 15 $\bar{X} \pm SD$ | Control group N = 18 $\bar{X} \pm SD$ |
|---|---|---|---|---|---|---|
| Pre-treatment | 31.09 ± 10.15 | 30.79 ± 11.25 | 31.37 ± 9.28 | 29.79 ± 12.23 | 30.17 ± 9.52 | 29.29 ± 21.25 |
| Day 5 | 17.06 ± 5.43 | 18.16 ± 6.48 | 18.83 ± 7.62 | 13.06 ± 7.49 | 15.83 ± 11.16 | 19.26 ± 17.49 |
| Day 11 | 9.34 ± 4.12 | 9.17 ± 4.11 | 8.80 ± 8.29 | 5.16 ± 4.07 | 7.80 ± 7.45 | 11.27 ± 6.18 |

During treatment, total testee grade of each group for HAMA anxious amount decreases day by day without bounce phenomenon after drug withdrawal. Total grade of prescription group D for withdrawal symptom decreases more quickly than other groups.

TABLE 23

Grade per day table of each group according to treatment emergent symptom scale (TESS)

| Course (Day) | Group A N = 15 $\bar{X} \pm SD$ | Group B N = 15 $\bar{X} \pm SD$ | Group C N = 15 $\bar{X} \pm SD$ | Group D N = 20 $\bar{X} \pm SD$ | Group E N = 15 $\bar{X} \pm SD$ | Control group N = 18 $\bar{X} \pm SD$ |
|---|---|---|---|---|---|---|
| 1 | 6.32 ± 2.12 | 8.55 ± 2.78 | 7.32 ± 1.16 | 5.57 ± 2.07 | 6.32 ± 1.16 | 3.32 ± 1.16 |
| 2 | 5.13 ± 1.45 | 6.12 ± 1.52 | 6.65 ± 1.16 | 4.09 ± 1.22 | 4.65 ± 1.16 | 3.12 ± 1.16 |
| 3 | 4.67 ± 2.37 | 5.09 ± 2.23 | 5.44 ± 1.34 | 4.09 ± 2.30 | 3.44 ± 1.34 | 2.42 ± 1.34 |
| 4 | 4.61 ± 2.34 | 4.91 ± 2.14 | 5.12 ± 2.17 | 4.91 ± 2.39 | 4.42 ± 2.17 | 3.62 ± 2.17 |
| 5 | 4.25 ± 2.12 | 5.55 ± 2.12 | 3.44 ± 1.34 | 3.55 ± 2.34 | 3.14 ± 1.34 | 2.54 ± 1.34 |
| 6 | 4.12 ± 2.37 | 5.12 ± 2.52 | 4.10 ± 0.88 | 3.00 ± 2.37 | 3.18 ± 0.88 | 2.89 ± 0.88 |
| 7 | 4.35 ± 2.25 | 4.35 ± 2.256 | 3.87 ± 1.00 | 3.13 ± 2.65 | 3.27 ± 1.00 | 2.67 ± 1.00 |
| 8 | 3.83 ± 1.23 | 3.83 ± 1.30 | 3.64 ± 1.16 | 3.73 ± 1.85 | 2.23 ± 1.16 | 2.24 ± 1.16 |
| 9 | 4.31 ± 1.35 | 4.31 ± 1.35 | 3.65 ± 1.06 | 2.55 ± 1.75 | 3.15 ± 1.06 | 2.25 ± 1.06 |
| 10 | 3.57 ± 1.26 | 3.80 ± 1.24 | 2.32 ± 1.73 | 2.00 ± 1.84 | 2.68 ± 1.732 | 2.88 ± 1.73 |

Adverse reaction grade of prescription group D and group E is obviously less than other groups after treatment. After overall assessment, curative effect of prescription group D (Radix Stephaniae Epigaeae) is better than group E (total alkaloid of Radix Stephaniae Epigaeae), and also is better than group B (Caulis Fibraureae) and group C (Radix Stephaniae Japonicae), therefore choose group D at last.

Experiment 10

Influence of Total Alkaloids of Radix Stephaniae Epigaeae for Intravenous Self-Administration Relapse Behavior of Cocaine Addiction Rat Because there is main heroin addiction in Chinese and the Asian area, but there is main cocaine abuse on international, the inventor carry on cocaine intravenous self-administration experiment in National Institute on Drug Abuse in National Institutes of Health (NIH/NIDA), at the same time, observe the intervention function relapse behavior of induced by environment with total alkaloids of Radix Stephaniae Epigaeae.

Administration route: administration by iv 0.5 mg/kg hydrochloric cocaine, fixation ratio 2 (namely obtain one injection by press staff twice). After establish self-administration model, stochastically divide into 5 dosage group, observe once in every day, 3 hours every time, intraperitoneal injection total alkaloids of Radix Stephaniae Epigaeae 1, 3, 10, 20, 30 mg/kg at 30 minutes before every experiment. So 3-30 mg/kg can all inhibit cocaine intravenous self-administration dosage-dependence, and it indicates that total alkaloids of Radix Stephaniae Epigaeae have intervention function to psychic dependence and relapse behavior of cocaine addiction, show in FIG. 7, FIG. 8.

DETAILED DESCRIPTION OF EMBODIMENTS

Example 1

Figure 1:
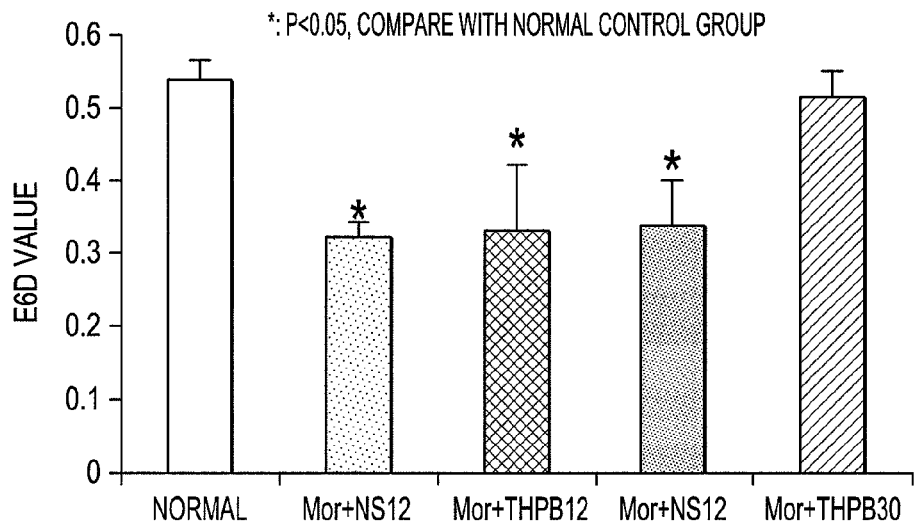
FIG. 1 is a chart depicting influence of total alkaloids of Radix Stephaniae Epigaeae for POMC mRNA gene expression in morphine dependence rat.
Figure 2:
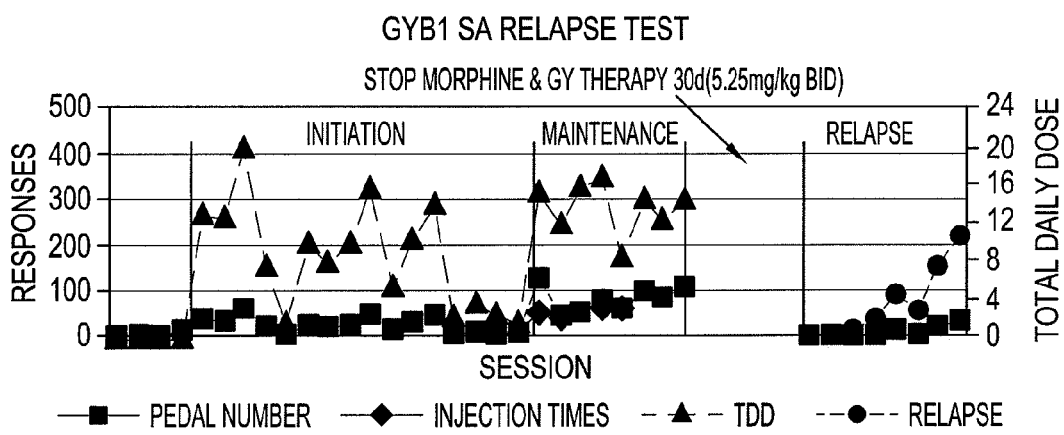
FIG. 2 is a record illustration depicting each index of the said invention pharmaceutical composition tablet about group A No. 1 rat experiment.
Figure 3:
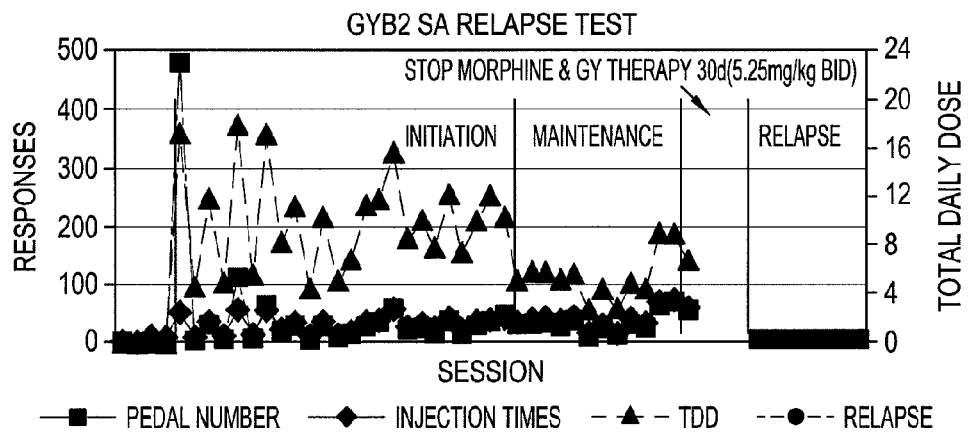
FIG. 3 is a record illustration depicting each index of the said invention pharmaceutical composition tablet about group B No. 2 rat experiment.
Figure 4:
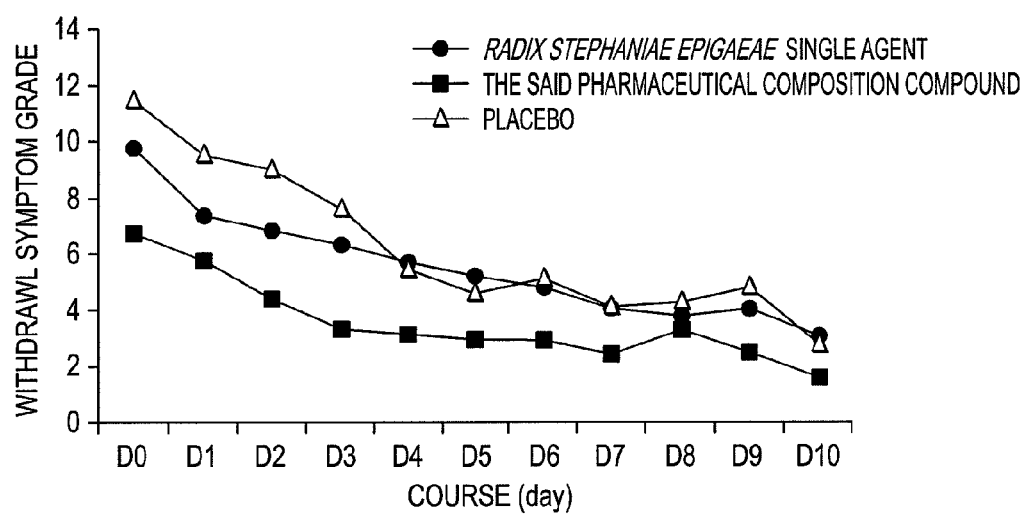
FIG. 4 is a mean graph depicting protracted withdrawal symptom after administration.
Figure 5:
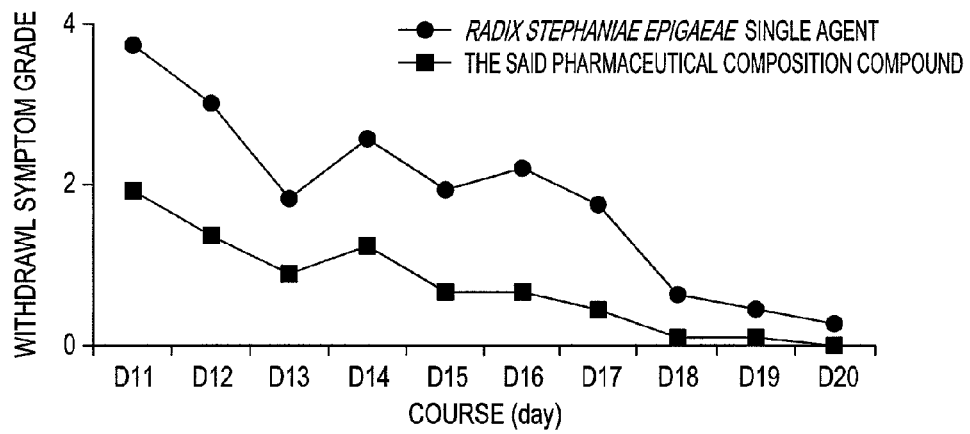
FIG. 5 is a graph depicting mean change of withdrawal symptom per day.
Figure 6:
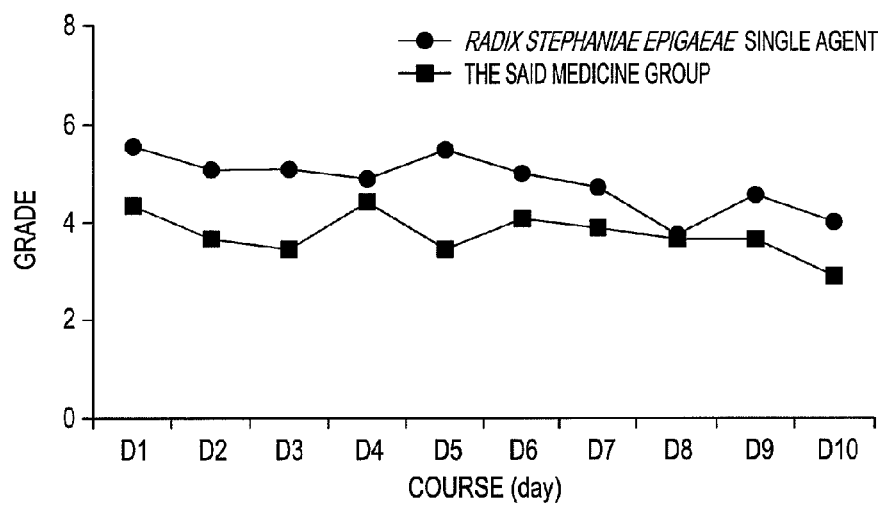
FIG. 6 is a graph depicting adverse reaction grade mean per day of two groups.
Figure 7:
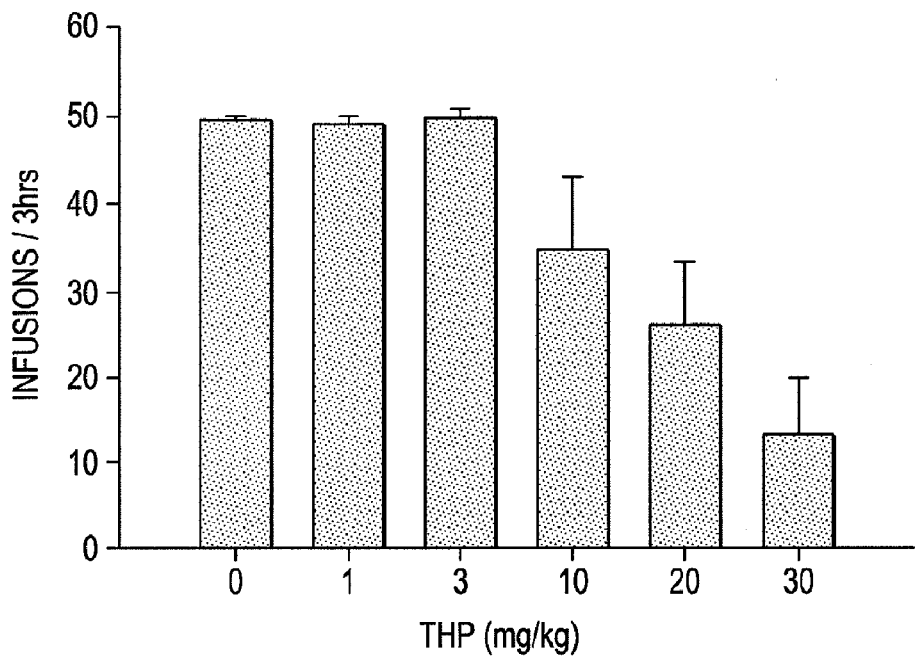
FIG. 7 is a chart depicting dosage dependence relation change of cocaine addiction relapse behavior.
Figure 8:
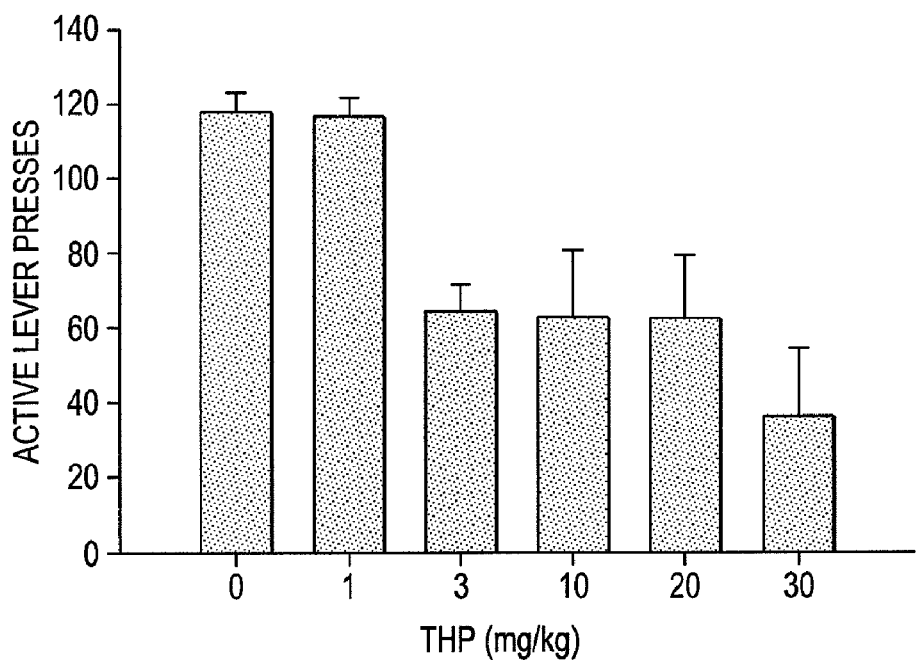
FIG. 8 is a chart depicting intervention to cocaine addiction relapse behavior.

Take 300 g Radix Ginseng, 1600 g Radix Stephaniae Epigaeae, 1000 g Radix Astragali, 500 g Radix Angelicae Sinensis and 300 g Radix Ophiopogonis, add 60% ethanol at 5 times amount to Radix Ginseng, Radix Angelicae Sinensis, then extract by reflux extraction twice, 2 hours each time; combine the ethanol extract, recover ethanol, concentrate to obtain the thick extract with relative density of 1.18-1.22 at 80° C., stand it by service; pulverize Radix Stephaniae Epigaeae to coarse power, add 5 times amount ethanol of stating material's, extract by reflux extraction twice, 2 hours each time, filter, combine the filtrates of ethanol extract, recover ethanol and concentrate to obtain the thick extract with relative density of 1.18-1.22 at 80° C.; acidify this thick extract until the pH value up to 2-3 by 5% HCl solution, filter, basify the filtrate until the pH value up to 9-10 by 10% NaOH solution, stand and collect the precipitate, wash the precipitate with water by filter, take the precipitate, dry it, stand it by service; decoct Radix Astragali and Radix Ophiopogonis with water at 6 times amount for three times, 1 hour each time, combine all the decoction, filter, concentrate the filtrate to obtain the thick extract with relative density of 1.18-1.22 at 80° C., add ethanol until ethanol concentration up to 70%, stand, filter, take the filtrates, recover ethanol and concentrate to obtain the thick extract with relative density of 1.18-1.22 at 80° C., stand it by service; take the said extract and the thick extract, combine them, add moderate amount sodium carboxymethyl starch, mix uniformly, recover solvent until dry, dry at 80° C., crush and sieve, make granules, press tablet, coating, that is.

Example 2

Air dry and pulverize Radix Stephaniae Epigaeae to get 300 g starting material powder, reflux with 85% ethanol for three times, add 1500 mL ethanol each time, reflux for 1 hour to gain tetrahydroprotoberberines (THPBs) alkaloid solution extracted from Radix Stephaniae Epigaeae, then recover ethanol, concentrate to obtain the thick extract 100 ml with relative density of 0.905 at 80° C. Acidify the thick extract until the pH value up to 2 by 5% HCl solution, filter off insoluble substances, basify the acid filtrate until the pH value up to 10 by 10% NaOH solution, stand, collect the precipitate, wash the precipitate with moderate amount water, take the precipitate, dry it, then dry the precipitate to obtain 14.7 g total alkaloids of Radix Stephaniae Epigaeae.

Dissolve the total alkaloids of Radix Stephaniae Epigaeae with 50 ml ethanol, stand at room temperature, and precipitate crystal 6.0 g. Recrystallize it again with ethanol to gain 3.5 g L-tetrahydropalmatine, and yield rate is 1.12%.

Take the said total alkaloids of Radix Stephaniae Epigaeae, add general adjuvant, produce to tablet, 0.35 g per tablet.

Example 3

Take 1 kg Radix Ginseng, 35 kg Radix Stephaniae Epigaeae, 7 kg Radix Astragali, 8 kg Radix Angelicae Sinensis and 2 kg Radix Ophiopogonis, A. Pulverize Radix Stephaniae Epigaeae to coarse power, add 40% ethanol at 6 times amount of stating material's, extract by reflux extraction for four times, 1 hour each time, filter, combine the filtrates of ethanol extract, recover ethanol and concentrate to obtain the thick extract with relative density of 1.18-1.30 at 80° C.; acidify this thick extract until the pH value up to 1 by 5% HCl solution, filter, basify the filtrate until the pH value up to 8 by 10% NaOH solution, stand, collect the precipitate, wash the precipitate with water by filter, take the precipitate, dry it, then obtain total alkaloids of Radix Stephaniae Epigaeae, stand it by service;

B. Add 40% ethanol at 8 times amount to Radix Ginseng, Radix Angelicae Sinensis, then extract by reflux extraction for one time, 1 hour each time, combine the ethanol extract, recover ethanol, concentrate to obtain the thick extract I with relative density of 1.18-1.30 at 80° C., stand it by service; decoct Radix Astragali and Radix Ophiopogonis with water at 5 times amount for one time, 1 hour each time, combine all the decoction, filter, concentrate the filtrate to obtain the thick extract with relative density of 1.18-1.30 at 80° C., add ethanol until ethanol concentration up to 50%, stand, filter, take the filtrates, recover ethanol and concentrate to obtain the thick extract II with relative density of 1.18-1.30 at 80° C., stand it by service;

C. Take the said total alkaloids of Radix Stephaniae Epigaeae, the thick extract I, the thick extract II, combine them, add general adjuvant, mix uniformly, according to usual process, produce to capsule.

Example 4

Take 8 kg Radix Ginseng, 12 kg Radix Stephaniae Epigaeae, 13 kg Radix Astragali, 5 kg Radix Angelicae Sinensis and 8 kg Radix Ophiopogonis, A. Pulverize Radix Stephaniae Epigaeae to coarse power, add 35% ethanol at 10 times amount of stating material's, extract by reflux extraction for one time, 3 hours each time, filter, combine the filtrates of ethanol extract, recover ethanol and concentrate to obtain the thick extract with relative density of 1.18-1.30 at 80° C.; acidify this thick extract until the pH value up to 4 by 3% HCl solution, filter, basify the filtrate until the pH value up to 11 by 8% NaOH solution, stand, collect the precipitate, wash the precipitate with water by filter, take the precipitate, dry it, then obtain total alkaloids of Radix Stephaniae Epigaeae, stand it by service;

B. Add 90% ethanol at 4 times amount to Radix Ginseng, Radix Angelicae Sinensis, then extract by reflux extraction from one to three times, 1 hour each time, combine the filtrates of ethanol extract, recover ethanol, then concentrate to obtain the thick extract I with relative density of 1.18-1.30 at 80° C., stand it by service; decoct Radix Astragali and Radix Ophiopogonis with water at 10 times amount for one time, 3 hours each time, combine all the decoction, filter, concentrate the filtrate to obtain the thick extract with relative density of 1.18-1.30 at 80° C., add ethanol until ethanol concentration up to 90%, stand, filter, take the filtrates, recover ethanol, then concentrate to obtain the thick extract II with relative density of 1.18-1.30 at 80° C., stand it by service;

C. Take the said total alkaloids of Radix Stephaniae Epigaeae, the thick extract I, the thick extract II, combine them, add general adjuvant, mix uniformly, according to usual process, produce to sustained-release preparation.

Example 5

Take 5 kg Radix Ginseng, 26 kg Radix Stephaniae Epigaeae, 20 kg Radix Astragali, 5 kg Radix Angelicae Sinensis and 5 kg Radix Ophiopogonis, A. Pulverize Radix Stephaniae Epigaeae to coarse power, add 70% ethanol at 6 times amount of stating material's, extract by reflux extraction for three times, 2 hours each time, filter, combine the filtrates of ethanol extract, recover ethanol, concentrate to obtain the thick extract with relative density of 1.18-1.30 at 80° C.; acidify this thick extract until the pH value up to 2 by 12% HCl solution, filter, basify the filtrate until the pH value up to 9 by 12% NaOH solution, stand, collect the precipitate, wash the precipitate with water by filter, take the precipitate, dry it, then obtain total alkaloids of Radix Stephaniae Epigaeae, stand it by service;

B. Add 80% ethanol at 8 times amount to Radix Ginseng, Radix Angelicae Sinensis, then extract by reflux extraction for two times, 2 hours each time, combine the filtrates of ethanol extract, recover ethanol, then concentrate to obtain the thick extract I with relative density of 1.18-1.30 at 80° C., stand it by service; decoct Radix Astragali and Radix Ophiopogonis with water at 6 times amount for three times, 1 hour each time, combine all the decoction, filter and concentrate the filtrate to obtain the thick extract with relative density of 1.18-1.30 at 80° C., add ethanol until ethanol concentration up to 60%, stand, filter, take the filtrates, recover ethanol, then concentrate to obtain the thick extract II with relative density of 1.18-1.30 at 80° C., stand it by service;

C. Take the said total alkaloids of Radix Stephaniae Epigaeae, the thick extract I, the thick extract II, combine them, add general adjuvant, mix uniformly, according to usual process, produce oral liquid.

Example 6

Take 3 kg Radix Ginseng, 16 kg Radix Stephaniae Epigaeae, 10 kg Radix Astragali, 5 kg Radix Angelicae Sinensis and 3 kg Radix Ophiopogonis, according to usual process, produce freeze-dry injection, 0.1 g per dosage.

Example 7

Take 8 kg Radix Ginseng, 40 kg Radix Stephaniae Epigaeae, 25 kg Radix Astragali, 10 kg Radix Angelicae Sinensis and 8 kg Radix Ophiopogonis, according to usual process, produce injection, 0.5 ml per dosage.

Example 8 is Take 100 g Radix Ginseng, 3500 g Radix Stephaniae Epigaeae, 700 g Radix Astragali, 800 g Radix Angelicae Sinensis and 200 g Radix Ophiopogonis. Extract according to example 1 method, add general adjuvant, according to usual process, produce capsule, pack, that is.

Example 9

Take 500 g Radix Ginseng, 2600 g Radix Stephaniae Epigaeae, 2000 g Radix Astragali, 500 g Radix Angelicae Sinensis and 500 g Radix Ophiopogonis. Extract according to example 1 method, add general adjuvant, according to usual process, produce granule, pack, that is.

Example 10

Take 30 g ethanol extract of Radix Ginseng, 60 g total alkaloids of Radix Stephaniae Epigaeae, 100 g ethanol extract of Radix Astragali, 80 g water extract of Radix Angelicae Sinensis and 60 g water extract of Radix Ophiopogonis. Extract according to example 1 method, add general adjuvant, according to usual process, produce oral liquid, pack, that is.

Example 11

Take 42 g ethanol extract of Radix Ginseng, 40 g total alkaloids of Radix Stephaniae Epigaeae, 140 g ethanol extract of Radix Astragali, 120 g water extract of Radix Angelicae Sinensis and 42 g water extract of Radix Ophiopogonis. Combine them, add moderate amount sodium carboxymethyl starch, mix uniformly, recover solvent until dry, dry at 80° C., crush and sieve, make granules, press tablet, coating, that is.

Example 12

Take 5-15 kg ethanol extract of Radix Ginseng, 20-40 kg ethanol extract of Radix Angelicae Sinensis, 5-15 kg total alkaloids of Radix Stephaniae Epigaeae, 20-60 kg water extract of Radix Astragali, and 5-15 kg water extract of Radix Ophiopogonis; according to usual process, produce freeze-dry injection, 0.1 g per dosage.

Example 13 is Take 6 kg ethanol extract of Radix Ginseng, 35 kg ethanol extract of Radix Angelicae Sinensis, 6 kg total alkaloids of Radix Stephaniae Epigaeae, 55 kg water extract of Radix Astragali, and 6 kg water extract of Radix Ophiopogonis; according to usual process, produce injection, 0.5 ml per dosage.

Example 14

Take 12 kg ethanol extract of Radix Ginseng, 25 kg ethanol extract of Radix Angelicae Sinensis, 12 kg total alkaloids of Radix Stephaniae Epigaeae, 25 kg water extract of Radix Astragali, and 12 kg water extract of Radix Ophiopogonis; according to usual process, produce capsule, 0.35 g per dosage.

Example 15

Take 10 kg ethanol extract of Radix Ginseng, 30 kg ethanol extract of Radix Angelicae Sinensis, 10 kg total alkaloids of Radix Stephaniae Epigaeae, 30 kg water extract of Radix Astragali, and 10 kg water extract of Radix Ophiopogonis; according to usual process, produce granule, 10 g per package.

Example 16

Take 11 kg ethanol extract of Radix Ginseng, 31 kg ethanol extract of Radix Angelicae Sinensis, 10 kg total alkaloids of Radix Stephaniae Epigaeae, 36.5 kg water extract of Radix Astragali, and 11 kg water extract of Radix Ophiopogonis; according to usual process, produce tablet, 0.35 g per tablet.

Example 17

Take 5 kg ethanol extract of Radix Ginseng, 16 kg ethanol extract of Radix Angelicae Sinensis, 20 kg total alkaloids of Radix Stephaniae Epigaeae, 40 kg water extract of Radix Astragali and 19 kg water extract of Radix Ophiopogonis; according to usual process, produce granule, 10 g per package.

Example 18

Take 15 kg ethanol extract of Radix Ginseng, 30 kg ethanol extract of Radix Angelicae Sinensis, 15 kg total alkaloids of Radix Stephaniae Epigaeae, 30 kg water extract of Radix Astragali, and 10 kg water extract of Radix Ophiopogonis; according to usual process, produce to capsule, 0.35 g per dosage.

Example 19

Identification include one of or several following methods:

A. Take 4 g freeze-dry injection of the example 6 pharmaceutical composition, grind fine, add methanol 50 ml, heat and reflux for 30 minutes, take it out, stand it cold, filter, evaporate filtrate 20 ml until dry, add 10 ml water and 5 drops hydrochloric acid into residue, shake up, extract twice by adding ethyl ether, 15 ml each time, combine ethyl ether extract, stand it by service; add ammonia to water layer until pH≈10, shake up, extract twice by adding chloroform, 20 ml each time, remove chloroform extract, extract for three times by adding n-butyl alcohol saturated with water to water layer, 20 ml each time, combine n-butyl alcohol extract, wash for three times by adding ammonia reagent, 10 ml dosage each time, take n-butyl alcohol extract, evaporate until dry, dissolve residue by add 1 ml methanol into it, as test sample solution; take Ginsenoside Rb1 and Ginsenoside Rg1 respectively as reference substance, add methanol to produce mix solution containing 1 mg reference substance per 1 ml respectively, as reference substance solution;

According to the thin layer Chromatography test, 5~10 μl each of the said two solutions were loaded onto the same TLC plate of silica gel G respectively, the upper layer solution is a mixture of n-butyl alcohol, ethyl acetate and water (4:1:5), according to ratio 10:1, a mix solution of this upper layer solution and methanol is used as developer, in developing, the development chamber is saturated by ammonia for 30 minutes, and developed distance is more than 15 cm, the plate was removed and air dried, and sprayed with ethanol solution of 10% sulfuric acid, then heated in 105° C. until visualize the chromatogram, the chromatogram produced by the test sample solution showed the same color spots as that displayed by the two reference substance solutions in their respectively corresponding areas;

B. Take astragaloside reference substance, add methanol to produce mix solution containing 1 mg reference substance per 1 ml, as reference substance solution, according to the thin layer Chromatography test, 5~10 μl each of reference substance solutions and test sample solutions produced by the identification method A are respectively loaded onto the same TLC plate of silica gel G, the upper layer solution is a mixture of n-butyl alcohol, ethyl acetate and water (4:1:5), according to ratio 10:1, a mix solution of this upper layer solution and methanol is used as developer, in developing, the development chamber is saturated by ammonia for 30 minutes, and developed distance is more than 15 cm, the plate was removed and air dried, and sprayed with ethanol solution of 10% sulfuric acid, then heated in 105° C. until visualize the chromatogram, the chromatogram produced by the test sample solution showed the same color spots as that displayed by the reference substance solution in its respectively corresponding area;

C. Produce ethyl ether extract according to the identification A method, evaporate solvent to dry, dissolve residue by adding 1 ml ethyl acetate, as test sample solution; take another 0.5 g reference medicine material of Radix Angelicae Sinensis, add ethyl ether 20 ml, heat and reflux for 1 hour, filter, evaporate ethyl ether in filtrate to dry, produce reference starting material solution by same method; according to the thin layer Chromatography test, 5~10 μl each of the said two solutions is loaded onto the same TLC plate of silica gel G respectively, a mixture of hexane and ethyl acetate (9:1) is used as developer, after development, the plate was removed and dried in air, and it was exam under 365 nm ultraviolet lamp, the chromatogram produced by the sample solution showed the same color spots as that displayed by the reference substance solution in its respectively corresponding areas;

D. Take 2 g tablet of a example 18 pharmaceutical composition, grind fine, decoct by adding water 100 ml for 30 minutes until rest volume up to 20 ml, stand it cold, add methanol until methanol content up to 50%, shake up, stay for 1 hour at lower than 10° C., filter, pressure reduction concentrate the filtrate to dry, dissolve the residue by adding 10 ml water, add 2 ml hydrochloric acid, shake up, reflux with boil water bath for 1 hour, take out and stand it cold, extract twice with ethyl ether, dosage 25 ml, combine ethyl ether extract, stand for 30 minutes, evaporate solvent until dry, dissolve residue by adding 1 ml methanol, shake up, as test sample solution;

take another 0.5 g reference medicine material of Radix Ophiopogonis, add water 20-30 ml, boil for 10 minutes, filter, produce reference starting material solution by same method; according to the thin layer Chromatography test, 2~5 μl each of the said two solutions is loaded onto the same TLC plate of silica gel G respectively, a mixture of chloroform and acetone (4:1) is used as developer, after development, the plate was removed and air dried, and sprayed with ethanol solution of 10% sulfuric acid, then heated in 105° C. until visualize the chromatogram, the chromatogram produced by the test sample solution showed the same color spots as that displayed by the reference substance solutions in its respectively corresponding areas.

Content determination in quality control method is as follows:

An Applicability Test of Chromatogram Condition and System

Use octadecylsilanized silica gel as packing; add ammonia 0.025 mol/L into potassium dihydrogen phosphate and acetonitrile (1:1) solution until as the mobile phase; detection wavelength is 225 nm, theoretical plate number counted according to (−) tetrahydropalmatine peak is not less than 3000;

Preparation of Reference Substance Solution

Pressure reduction dry 5.5 mg (−) tetrahydropalmatine reference substance at 60° C. until constant weight, weight it accurately, put it into 10 ml volumetric flask, dissolve by methanol, dilute to the volume, shake up, measure 1 ml said solution accurately, put it into 10 ml volumetric flask, and dilute with the mobile phase to the volume, shake up, that is;

Preparation of Test Sample Solution

Accurately weight 0.35 g tablet of said pharmaceutical composition, grind fine, put it into conical flask, add 50 ml methanol accurately, shake up, weight it up, put it into ultrasonic cleaner, deal with ultrasound for 30 minutes, take it out, complement weight with methanol, shake up, filter, abandon first filtrate, measure 1 ml the following filtrate accurately and put it into 10 ml volumetric flask, dilute with the mobile phase to the volume, shake up, filter it with 0.45 μm microporous membrane filter, take the following filtrate as test sample solution;

Determination Method

Accurately suck reference substance solution and test sample solution 10 μl respectively, inject into liquid chromatogram instrument, determine, that is;

(−) Tetrahydropalmatine regarded as Radix Stephaniae Epigaeae is not less than 20 mg in each of 0.35 g tablet of the said pharmaceutical composition.

Example 20

Identification include one of or several following methods:

A. Take 5 g example 9 granule of the pharmaceutical composition, grind fine, add methanol 50 ml, heat and reflux for 30 minutes, take it out, stand it cold, filter, evaporate filtrate 20 ml until dry, add 10 ml water and 5 drops hydrochloric acid into residue, shake up, extract twice by adding ethyl ether, 15 ml each time, combine ether extract, stand it by service; add ammonia to water layer until 10, shake up, extract twice by adding chloroform, 20 ml each time, remove chloroform extract, extract for three times by adding n-butyl alcohol saturated with water to water layer, 20 ml each time, combine n-butyl alcohol extract, wash for three times by adding ammonia reagent, 10 ml dosage each time, take n-butyl alcohol extract, evaporate until dry, dissolve residue by add 1 ml methanol into it, as test sample solution; take Ginsenoside Rb1 and Ginsenoside Rg1 respectively as reference substance, add methanol to produce mix solution containing 1 mg reference substance per 1 ml respectively, as reference substance solution;

According to the thin layer Chromatography test, 5~10 μl each of the said two solutions were loaded onto the same TLC plate of silica gel G respectively, the upper layer solution is a mixture of n-butyl alcohol, ethyl acetate and water (4:1:5), according to ratio 10:1, a mix solution of this upper layer solution and methanol is used as developer, in developing, the development chamber is saturated by ammonia for 30 minutes, and developed distance is more than 15 cm, the plate was removed and air dried, and sprayed with ethanol solution of 10% sulfuric acid, then heated in 105° C. until visualize the chromatogram, the chromatogram produced by the test sample solution showed the same color spots as that displayed by the two reference substance solutions in their respectively corresponding areas;

B. Take astragaloside reference substance, add methanol to produce mix solution containing 1 mg reference substance per 1 ml, as reference substance solution, according to the thin layer Chromatography test, 5~10 μl each of reference substance solutions and test sample solutions produced by the identification method A are respectively loaded onto the same TLC plate of silica gel G, the upper layer solution is a mixture of n-butyl alcohol, ethyl acetate and water (4:1:5), according to ratio 10:1, a mix solution of this upper layer solution and methanol is used as developer, in developing, the development chamber is saturated by ammonia for 30 minutes, and developed distance is more than 15 cm. The plate was removed and air dried, and sprayed with ethanol solution of 10% sulfuric acid, then heated in 105° C. until visualize the chromatogram, the chromatogram produced by the test sample solution showed the same color spots as that displayed by the reference substance solution in its respectively corresponding area;

C. Produce ethyl ether extract according to the identification A method, evaporate solvent to dry, dissolve residue by adding 1 ml ethyl acetate, as test sample solution; take another 0.5 g reference medicine material of Radix Angelicae Sinensis, add ethyl ether 20 ml, heat and reflux for 1 hour, filter, evaporate ethyl ether in filtrate to dry, produce reference starting material solution by same method; according to the thin layer Chromatography test, 5~10 μl each of the said two solutions is loaded onto the same TLC plate of silica gel G respectively, a mixture of hexane and ethyl acetate (9:1) is used as developer. After development, the plate was removed and dried in air, and it was exam under 365 nm ultraviolet lamp, the chromatogram produced by the sample solution showed the same color spots as that displayed by the reference substance solution in its respectively corresponding areas;

D. Take 3.5 g example 8 capsule of a pharmaceutical composition, grind fine, decoct by adding water 100 ml for 30 minutes until rest volume up to 20 ml, stand it cold, add methanol until methanol content up to 50%, shake up, stay for 1 hour at lower than 10° C., filter, pressure reduction concentrate the filtrate to dry, dissolve the residue by adding 10 ml water, add 2 ml hydrochloric acid, shake up, reflux with boil water bath for 1 hour, take out and stand it cold, extract twice by ethyl ether, dosage 25 ml, combine ethyl ether extract, stand for 30 minutes, evaporate solvent until dry, dissolve residue by adding 1 ml methanol, shake up, as test sample solution; take another 0.5 g reference medicine material of Radix Ophiopogonis, add water 20-30 ml, boil for 10 minutes, filter, produce reference starting material solution by same method; according to the thin layer Chromatography test, 2~5 μl each of the said two solutions is loaded onto the same TLC plate of silica gel G respectively, a mixture of chloroform and acetone (4:1) is used as developer. After development, the plate was removed and air dried, and sprayed with ethanol solution of 10% sulfuric acid, then heated in 105° C. until visualize the chromatogram, the chromatogram produced by the test sample solution showed the same color spots as that displayed by the reference substance solution in its respectively corresponding areas.

Example 21

Content determination in quality control method is as follows:

An Applicability Test of Chromatogram Condition and System

Use octadecylsilanized silica gel as packing; add ammonia 0.025 mol/L into potassium dihydrogen phosphate and acetonitrile (1:1) solution until as the mobile phase; detection wavelength is 225 nm, theoretical plate number counted according to (−) tetrahydropalmatine peak is not less than 3000;

Preparation of Reference Substance Solution

Pressure reduction dry 5.5 mg (−) tetrahydropalmatine reference substance at 60° C. until constant weight, weight it accurately, put it into 10 ml volumetric flask, dissolve by methanol, dilute to the volume, shake up, measure 1 ml the said solution accurately, put it into 10 ml volumetric flask, and dilute with the mobile phase to the volume, shake up, that is;

Preparation of Test Sample Solution

Accurately weight 0.45 g example 14 capsule of said pharmaceutical composition, grind fine, put it into conical flask, add 50 ml methanol accurately, shake up, weight it up, put it into ultrasonic cleaner, deal with ultrasound for 30 minutes, take it out, complement weight with methanol, shake up, filter, abandon first filtrate, measure 1 ml the following filtrate accurately and put it into 10 ml volumetric flask, dilute with the mobile phase to the volume, shake up, filter it with 0.45 μm microporous membrane filter, take the following filtrate as test sample solution;

Determination Method

Accurately suck reference substance solution and test sample solution 10 μl respectively, inject into liquid chromatogram instrument, determine, that is;

(−) Tetrahydropalmatine regarded as Radix Stephaniae Epigaeae is not less than 20 mg in each of 0.45 g capsule of said pharmaceutical composition.

Example 22

Identification method is as follows:

A. Take 4 g example 4 sustained-release tablet of the pharmaceutical composition, add methanol 50 ml, heat and reflux for 30 minutes, take it out, stand it cold, filter, evaporate filtrate 20 ml until dry, add 10 ml water and 5 drops hydrochloric acid into residue, shake up, extract twice by adding ethyl ether, 15 ml each time, combine ether extract, stand it by service; add ammonia to water layer until pH≈10, shake up, extract twice by adding chloroform, 20 ml each time, remove chloroform extract, extract for three times by adding n-butyl alcohol saturated with water to water layer, 20 ml each time, combine n-butyl alcohol extract, wash for three times by adding ammonia reagent, 10 ml dosage each time, take n-butyl alcohol extract, evaporate until dry, dissolve residue by add 1 ml methanol into it, as test sample solution; take Ginsenoside Rb1 and Ginsenoside Rg1 respectively as reference substance, add methanol to produce mix solution containing 1 mg reference substance per 1 ml respectively, as reference substance solution;

According to the thin layer Chromatography test, 5~10 μl each of the said two solutions were loaded onto the same TLC plate of silica gel G respectively, the upper layer solution is a mixture of n-butyl alcohol, ethyl acetate and water (4:1:5); according to ratio 10:1, a mix solution of this upper layer solution and methanol is used as developer. In developing, the development chamber is saturated by ammonia for 30 minutes, and developed distance is more than 15 cm, the plate was removed and air dried, and sprayed with ethanol solution of 10% sulfuric acid, then heated in 105° C. until visualize the chromatogram, the chromatogram produced by the test sample solution showed the same color spots as that displayed by the two reference substance solutions in their respectively corresponding areas;

B. Take astragaloside reference substance, add methanol to produce mix solution containing 1 mg reference substance per 1 ml, as reference substance solution; according to the thin layer Chromatography test, 5~10 μl each of reference substance solutions and test sample solutions produced by the identification method A are respectively loaded onto the same TLC plate of silica gel G. The upper layer solution is a mixture of n-butyl alcohol, ethyl acetate and water (4:1:5); according to ratio 10:1, a mix solution of this upper layer solution and methanol is used as developer, in developing, the development chamber is saturated by ammonia for 30 minutes, and developed distance is more than 15 cm, the plate was removed and air dried, and sprayed with ethanol solution of 10% sulfuric acid, then heated in 105° C. until visualize the chromatogram, the chromatogram produced by the test sample solution showed the same color spots as that displayed by the reference substance solution in its respectively corresponding area, C. Produce ethyl ether extract according to the identification A method, evaporate solvent to dry, dissolve residue by adding 1 ml ethyl acetate, as test sample solution; take another 0.5 g reference medicine material of Radix Angelicae Sinensis, add ethyl ether 20 ml, heat and reflux for 1 hour, filter, evaporate ethyl ether in filtrate to dry, produce reference starting material solution by same method; According to the thin layer Chromatography test, 5~10 μl each of the said two solutions is loaded onto the same TLC plate of silica gel G respectively, a mixture of hexane and ethyl acetate (9:1) is used as developer, after development, the plate was removed and dried in air, and it was exam under 365 nm ultraviolet lamp, the chromatogram produced by the sample solution showed the same color spots as that displayed by the reference substance solutions in its respectively corresponding areas;

D. Take 1.75 g example 15 granule, grind fine, decoct by adding water 100 ml for 30 minutes until rest volume up to 20 ml, stand it cold, add methanol until methanol content up to 50%, shake up, stay for 1 hour at lower than 10° C., filter, pressure reduction concentrate the filtrate to dry, dissolve the residue by adding 10 ml water, add 2 ml hydrochloric acid, shake up, reflux with boil water bath for 1 hour, take out and stand it cold, extract twice by ethyl ether, dosage 25 ml, combine ethyl ether extract, stand for 30 minutes, evaporate solvent until dry, dissolve residue by adding 1 ml methanol, shake up, as test sample solution;

take another 0.5 g reference drug of Radix Ophiopogonis, add water 20-30 ml, boil for 10 minutes, filter, produce reference medicine material solution by same method; according to the thin layer Chromatography test, 2~5 μl each of the said two solutions is loaded onto the same TLC plate of silica gel G respectively, a mixture of chloroform and acetone (4:1) is used as developer, after development, the plate was removed and air dried, and sprayed with ethanol solution of 10% sulfuric acid, then heated in 105° C. until visualize the chromatogram, the chromatogram produced by the test sample solution showed the same color spots as that displayed by the reference substance solution in its respectively corresponding areas.

Content determination in quality control method is as follows:

An Applicability Test of Chromatogram Condition and System

Use octadecylsilanized silica gel as packing; add ammonia 0.025 mol/L into potassium dihydrogen phosphate and acetonitrile (1:1) solution until as the mobile phase; detection wavelength is 225 nm, theoretical plate number counted according to (−) tetrahydropalmatine peak is not less than 3000;

Preparation of Reference Substance Solution

Pressure reduction dry 5.5 mg (−) tetrahydropalmatine reference substance at 60° C. until constant weight, weight it accurately, put it into 10 ml volumetric flask, dissolve by methanol, dilute to the volume, shake up, measure 1 ml the said solution accurately, put it into 10 ml volumetric flask, and dilute with the mobile phase to the volume, shake up, that is;

Preparation of Test Sample Solution

Accurately weight 0.4 g example 17 granule of the said pharmaceutical composition, grind fine, put it into conical flask, add 50 ml methanol accurately, shake up, weight it up, put it into ultrasonic cleaner, deal with ultrasound for 30 minutes, take it out, complement weight with methanol, shake up, filter, abandon first filtrate, measure 1 ml the following filtrate accurately and put it into 10 ml volumetric flask, dilute with the mobile phase to the volume, shake up, filter it with 0.45 μm microporous membrane filter, take the following filtrate as test sample solution;

Determination Method

Accurately suck reference substance solution and test sample solution 10 μl respectively, inject into liquid chromatogram instrument, determine, that is.

(−) Tetrahydropalmatine regarded as Radix Stephaniae Epigaeae is not less than 20 mg in each of 0.4 g granule of the said pharmaceutical composition.

Example 23

Pulverize Radix Stephaniae Epigaeae to coarse power, add 5 times amount ethanol of stating material's, then extract by reflux extraction for two times, 2 hours each time, filter, combine the filtrates of ethanol extract, recover ethanol and concentrate to obtain the thick extract with relative density of 1.18-1.30 at 80° C.; acidify this thick extract until the pH value up to 2-3 by 5% A HCl solution, filter, basify the filtrate until the pH value up to 9-10 by 10% NaOH solution, stand and collect the precipitate, wash the precipitate with water by filter, take the precipitate, dry it, then obtain total alkaloids from Radix Stephaniae Epigaeae, add general adjuvant, produce pill.

Example 24

Pulverize Radix Stephaniae Epigaeae to 3 kg coarse power, add 6 times amount 85% ethanol of stating material's, then extract by reflux extraction for two times, 3 hours each time, filter, combine the filtrates of ethanol extract, recover ethanol, then concentrate to obtain the thick extract with relative density of 1.18-1.30 at 80° C.; acidify this thick extract until the pH value up to 1 by 4% HCl solution, filter, basify the filtrate until the pH value up to 11 by 8-20% NaOH solution, stand, collect the precipitate, wash the precipitate with water by filter, take the precipitate, dry it, then obtain total alkaloids from Radix Stephaniae Epigaeae; add general adjuvant, produce honey refined extract.

Example 25

Pulverize Radix Stephaniae Epigaeae to 3 kg coarse power, add 9 times amount 40% ethanol of stating material's, then extract by reflux extraction for four times, 1 hour each time, filter, combine the filtrates of ethanol extract, recover ethanol, then concentrate to obtain the thick extract with relative density of 1.18-1.30 at 80° C.; acidify this thick extract until the pH value up to 3 by 5% HCl solution, filter, basify the filtrate until the pH value up to 9 by 8-20% NaOH solution, stand, collect the precipitate, wash the precipitate with water by filter, take the precipitate, dry it, then obtain total alkaloids from Radix Stephaniae Epigaeae; add general adjuvant, produce injection.

Example 26

Pulverize Radix Stephaniae Epigaeae to 3 kg coarse power, add 8 times amount 50% ethanol of stating material's, then extract by reflux extraction for three times, 2 hours each time, filter, combine the filtrates of ethanol extract, recover ethanol, then concentrate to obtain the thick extract with relative density of 1.18-1.30 at 80° C.; acidify this thick extract until the pH value up to 2.5 by 12% HCl solution, filter, basify the filtrate until the pH value up to 9.5 by 15% NaOH solution, stand, collect the precipitate, wash the precipitate with water by filter, take the precipitate, dry it, then obtain total alkaloids from Radix Stephaniae Epigaeae; add general adjuvant, produce rapid-release preparation.

What is claimed:

1. A method of treating drug addiction, comprising the steps of:
    pulverizing Radix Stephaniae Epigaeae to powder as a starting material,
    adding 35-100% ethanol at 4-10 times the amount of the starting material by weight,
    extracting by reflux extraction from one to four times, 1-3 hours each time,
    filtering the extract,
    combining the filtrates of ethanol extract,
    recovering ethanol from the filtrates,
    concentrating the recovered ethanol to obtain a thick extract with relative density of 1.18-1.30 at 80° C.;
    acidifying said thick extract with 3-18% HCl solution until the pH value is 1-4,
    filtering the acidified thick extract,
    basifying the filtrate with 8-20% NaOH solution until the pH value is 8-11,
    allowing the basified filtrate to stand,
    collecting a precipitate of the basified filtrate,
    washing the precipitate with water,
    drying the precipitate in order to obtain an extract of Radix Stephaniae Epigaeae, and
    administering an effective amount of a medicine comprising the extract of Radix Stephaniae Epigaeae to a patient in need thereof.

2. The method of claim 1, wherein the medicine raises expression of Penk mRNA or expression of POMC mRNA in arcuate nucleus.

* * * * *